(12) United States Patent
Sakaguchi et al.

(10) Patent No.: US 11,578,067 B2
(45) Date of Patent: Feb. 14, 2023

(54) COMPOUND, AND METHOD FOR PRODUCING REGULATORY T CELLS

(71) Applicants: Kyoto University, Kyoto (JP); Astellas Pharma Inc., Tokyo (JP)

(72) Inventors: Shimon Sakaguchi, Kyoto (JP); Naganari Ohkura, Kyoto (JP); Norihisa Mikami, Kyoto (JP); Shuh Narumiya, Kyoto (JP); Masahiko Akamatsu, Tokyo (JP); Guliang Xia, San Diego, CA (US); Hironori Harada, Tokyo (JP); Naoto Nakamura, Tokyo (JP); Satoru Ujihara, Tokyo (JP); Hisao Hamaguchi, Tokyo (JP)

(73) Assignees: KYOTO UNIVERSITY, Kyoto (JP); ASTELLAS PHARMA INC., Tokyo (JP)

( * ) Notice: Subject to any disclaimer, the term of this patent is extended or adjusted under 35 U.S.C. 154(b) by 655 days.

(21) Appl. No.: 16/479,229

(22) PCT Filed: Jan. 30, 2018

(86) PCT No.: PCT/JP2018/002826
§ 371 (c)(1),
(2) Date: Jul. 19, 2019

(87) PCT Pub. No.: WO2018/139660
PCT Pub. Date: Aug. 2, 2018

(65) Prior Publication Data
US 2019/0382403 A1 Dec. 19, 2019

Related U.S. Application Data

(60) Provisional application No. 62/491,279, filed on Apr. 28, 2017, provisional application No. 62/451,807, filed on Jan. 30, 2017.

(51) Int. Cl.
| | | |
|---|---|---|
| *C07D 471/04* | (2006.01) | |
| *A61K 35/17* | (2015.01) | |
| *C12N 5/0783* | (2010.01) | |
| *A61P 37/08* | (2006.01) | |
| *A61P 29/00* | (2006.01) | |
| *A61P 37/06* | (2006.01) | |
| *A61K 31/437* | (2006.01) | |
| *A61K 31/497* | (2006.01) | |
| *C12N 15/11* | (2006.01) | |

(52) U.S. Cl.
CPC .......... *C07D 471/04* (2013.01); *A61K 31/437* (2013.01); *A61K 31/497* (2013.01); *A61K 35/17* (2013.01); *A61P 29/00* (2018.01); *A61P 37/06* (2018.01); *A61P 37/08* (2018.01); *C12N 5/0637* (2013.01); *C12N 15/11* (2013.01); *C12N 2500/38* (2013.01); *C12N 2501/04* (2013.01); *C12N 2501/15* (2013.01); *C12N 2501/999* (2013.01)

(58) Field of Classification Search
None
See application file for complete search history.

(56) References Cited

U.S. PATENT DOCUMENTS

| 2009/0136470 A1 | 5/2009 | Cheroute et al. |
|---|---|---|
| 2009/0257988 A1 | 10/2009 | Horwitz et al. |

FOREIGN PATENT DOCUMENTS

| JP | 2009215284 A | 9/2009 |
|---|---|---|
| JP | 2010004853 A | 1/2010 |
| WO | 2005037197 A2 | 4/2005 |
| WO | 2005037198 A2 | 4/2005 |
| WO | 2006113837 A2 | 10/2006 |
| WO | 2007140222 A2 | 12/2007 |
| WO | 2013161408 A1 | 10/2013 |
| WO | 2014029726 A1 | 2/2014 |
| WO | 2018027082 A1 | 2/2018 |

OTHER PUBLICATIONS

Koehler et al., Development of a Potent, Specific CDK8 Kinase Inhibitor Which Phenocopies CDK8/19 Knockout Cells. ACS Medicinal Chemistry Letters, 2016, 7, 223-228.*
Vignali et al., How regulatory T cells work. Nature Reviews Immunology, 2008, 8, 523-532.*
Extended European Search Report issued in corresponding European Patent Application No. 18744360.1 dated Jun. 24, 2021 (6 pages).
Li et al., "Function of a Foxp3 cis-element in protecting regulatory T cell identity," Cell, 2014, 158(4): pp. 734-748.
Malinkova et al., "Cyclin-dependent kinase inhibitors for cancer therapy: a patent review (2009-2014)," Expert Opinion on Therapeutic Patents, vol. 25, No. 9 (2015), pp. 953-970.
International Search Report and Written Opinion issued in corresponding International Patent Application No. PCT/JP2018/002826 (with English translation of International Search Report) dated May 1, 2018 (16 pages).
Porter et al., "Cyclin-dependent kinase 8 mediates chemotherapy-induced tumor-promoting paracrine activities," PNAS, 2012, vol. 109, No. 34, pp. 13799-13804.

* cited by examiner

*Primary Examiner* — Po-Chih Chen
(74) *Attorney, Agent, or Firm* — Kilyk & Bowersox, P.L.L.C.

(57) ABSTRACT

Provided are a novel compound having CDK8 and/or CDK19 inhibitory activity, and a production method for Tregs. The treatment of T cells with a CDK8 and/or CDK19 inhibitor induces Foxp3 in the T cells. Foxp3$^+$ T cells can be induced by treating Foxp3$^-$ T cells with the CDK8 and/or CDK19 inhibitor in vitro. Thus, Tregs can be induced.

14 Claims, 19 Drawing Sheets

COMPOUND, AND METHOD FOR PRODUCING REGULATORY T CELLS

The present application claims priority from U.S. Provisional Patent Application No. 62/451,807 and U.S. Provisional Patent Application No. 62/491,279, which are incorporated herein by reference.

TECHNICAL FIELD

The present application is a National Stage Application of PCT/JP2018/002826, filed Jan. 30, 2018, which claims priority from U.S. Provisional Patent Application No. 62/451,807 and U.S. Provisional Patent Application No. 62/491,279, which are incorporated herein by reference.

BACKGROUND ART

Cyclin-dependent kinase 8 (CDK8) and its related isoform CDK19 each regulate transcriptional activity through phosphorylation of RNA polymerase 2 responsible for transcription. CDK8 was identified as an oncogene in melanoma (Nature 468, 1105-1109, 2010) and colorectal cancer (Nature 455, 547-551, 2008), and there is also a report that high expression of CDK8 is associated with progress of malignancy in colorectal cancer (Int. J. Cancer 126, 2863-2873, 2010). In addition, it is known that CDK8 maintains embryonic stem cell pluripotency, suggesting its relationship with a trait of cancer stem cells (Cancer Res. 72, 2129-2139, 2012). Therefore, a large number of CDK8 inhibitors and CDK19 inhibitors have been proposed as therapeutic drugs for various cancers, and as therapeutic drugs for autoimmune diseases and inflammatory diseases. Specifically, there are given, for example, compounds described in U.S. Pat. No. 8,598,344 B2, WO 2013/001310 A1, WO 2013/040153 A1, WO 2013/116786 A1, WO 2014/029726 A1, WO 2014/063778 A1, WO 2014/072435 A1, WO 2014/090692 A1, WO 2014/106606 A1, WO 2014/123900 A1, WO 2014/154723 A1, WO 2014/194245 A1, WO 2015/049325 A1, WO 2015/100420 A1, WO 2015/144290 A1, WO 2015/159937 A1, WO 2015/159938 A1, and WO 2016/009076 A1.

In an immune system, there is a subset of CD4$^+$ T cells called regulatory T cells (Tregs) having a function of suppressing immune responses. The Tregs play important roles in maintaining immune tolerance and immune homeostasis by regulating various pathological immune responses, such as autoimmunity, inflammation, and allergy. The Tregs include natural-occurring Tregs (nTregs), which develop in the thymus, and induced Tregs (iTregs), which are induced by an action of TGF-β in the periphery. Immune response-suppressing functions of those Tregs are defined by expression and maintenance of a transcription factor Foxp3 (Science, 299, 1057-1061 (2003), Immunological Reviews 212, 8-27 (2006), Nat. Immunol., 8, 457-462 (2007)).

There are proposals of a method of treating immune diseases involving enhancing or attenuating immune responses by targeting Tregs, and a cell therapy method using Tregs. Examples thereof include: using an immunosuppressant containing a geranylgeranylation inhibitor as an active ingredient for autoimmune diseases and inflammatory diseases (Patent Literature 1: JP 2009-215284 A); in vitro co-culturing CD4$^+$ naive cells and mast cells in the presence of interleukin-33 (IL-33) to produce Tregs, which are used as an immunosuppressant for suppressing onset of diseases such as allergic diseases and rheumatism and an organ transplant rejection reaction (Patent Literature 2: JP 2010-4853 A); bringing T cells into contact with transforming growth factor-beta (TGF-β) and retinoic acid to stimulate or increase differentiation to Tregs, which are used for autoimmune diseases and the like (Patent Literature 3: US 20090136470 A1); in vitro culturing CD4$^+$ T cells in the presence of interleukin-2 (IL-2), TGF-β1, and all-trans-retinoic acid (atRA or tretinoin) to induce CD8$^+$ Tregs, which are used for autoimmune diseases, malignant tumors, viral infections, and the like (Patent Literature 4: WO 2013/161408 A1); and ex vivo treating non-regulatory T cells with a regulatory composition containing a methyltransferase inhibitor to produce Tregs, which are used for treating autoimmune diseases and aberrant immune responses (Patent Literature 5: US 20090257988 A1).

However, further development of a Treg induction method is expected.

CITATION LIST

Patent Literature

[Patent literature 1] JP 2009-215284 A
[Patent literature 2] JP 2010-4853 A
[Patent literature 3] US 20090136470 A1
[Patent literature 4] WO 2013/161408 A1
[Patent literature 5] US 20090257988 A1

SUMMARY OF INVENTION

Technical Problem

The present invention provides a novel compound having CDK8 and/or CDK19 inhibitory activity, and a production method for Tregs.

Solution to Problem

The inventors of the present invention have made investigations on novel compounds each having CDK8 and/or CDK19 inhibitory activity, and in the course of the investigations, have found for the first time that a CDK8 and/or CDK19 inhibitor induces Foxp3 in T cells. The inventors have also found that CD4$^+$CD25$^+$ Foxp3$^+$ Tregs can be induced by treating CD4$^+$ CD25$^-$ Foxp3$^-$ T cells with the CDK8 and/or CDK19 inhibitor in vitro. The inventors have also found that CD8$^+$ Foxp3$^+$ Tregs can be induced by treating CD8$^+$ Foxp3$^-$ T cells with the CDK8 and/or CDK19 inhibitor in vitro. Thus, the inventors have completed the present invention.

The present invention includes the following.

(1) A compound selected from
4-[1-(2-methyl-1H-benzimidazol-5-yl)-1H-imidazo[4,5-c]pyridin-2-yl]-1,2,5-oxadiazol-3-amine and 3-{1-[1-(4-methoxyphenyl)piperidin-4-yl]-4-methyl-1H-imidazo[4,5-c]pyridin-2-yl}pyrazin-2-amine, or a salt, a hydrate, or a solvate thereof.

(2) A pharmaceutical composition for treating cancers, autoimmune diseases, inflammatory diseases, or allergic diseases, including as an active ingredient a compound selected from 4-[1-(2-methyl-1H-benzimidazol-5-yl)-1H-imidazo[4,5-c]pyridin-2-yl]-1,2,5-oxadiazol-3-amine and 3-{1-[1-(4-methoxyphenyl)piperidin-4-yl]-4-methyl-1H-imidazo[4,5-c]pyridin-2-yl}pyrazin-2-amine, or a salt, a hydrate, or a solvate thereof.

(3) A Foxp3 inducer for producing regulatory T cells from T cells, including as an active ingredient a compound having CDK8 and/or CDK19 inhibitory activity, or a salt, a hydrate, or a solvate thereof.

(4) The Foxp3 inducer according to the above-mentioned item (3), wherein the T cells include CD4$^+$ Foxp3$^-$ T cells.

(5) The Foxp3 inducer according to the above-mentioned item (3), wherein the T cells include CD4$^+$CD25$^-$ Foxp3$^-$ T cells.

(6) The Foxp3 inducer according to the above-mentioned item (3), wherein the T cells include CD8$^+$ Foxp3$^-$ T cells.

(7) The Foxp3 inducer according to any one of the above-mentioned items (3) to (6), wherein the compound having CDK8 and/or CDK19 inhibitory activity includes a compound shown in any one of the following items 1) to 3):
1) 4-[1-(2-methyl-1H-benzimidazol-5-yl)-1H-imidazo[4,5-c]pyridin-2-yl]-1,2,5-oxadiazol-3-amine;
2) 3-{1-[1-(4-methoxyphenyl)piperidin-4-yl]-4-methyl-1H-imidazo[4,5-c]pyridin-2-yl}pyrazin-2-amine; and
3) siRNA of CDK8 and/or CDK19.

(8) A production method for regulatory T cells, including treating T cells with a compound having CDK8 and/or CDK19 inhibitory activity, or a salt, a hydrate, or a solvate thereof.

(9) A production method for regulatory T cells, including subjecting T cells to T cell receptor (TCR) stimulation in the presence of a compound having CDK8 and/or CDK19 inhibitory activity, or a salt, a hydrate, or a solvate thereof.

(10) The production method for regulatory T cells according to the above-mentioned item (9), wherein the TCR stimulation is performed in the presence of TGF-β, rapamycin, or retinoic acid.

(11) The production method for regulatory T cells according to any one of the above-mentioned items (8) to (10), wherein the T cells include CD4$^+$ Foxp3$^-$ T cells.

(12) The production method for regulatory T cells according to any one of the above-mentioned items (8) to (10), wherein the T cells include CD4$^+$CD25$^-$ Foxp3$^-$ T cells.

(13) The production method for regulatory T cells according to any one of the above-mentioned items (8) to (10), wherein the T cells include CD8$^+$ Foxp3$^-$ T cells.

(14) The production method for regulatory T cells according to any one of the above-mentioned items (8) to (13), wherein the compound having CDK8 and/or CDK19 inhibitory activity includes a compound shown in any one of the following items 1) to 3):
1) 4-[1-(2-methyl-1H-benzimidazol-5-yl)-1H-imidazo[4,5-c]pyridin-2-yl]-1,2,5-oxadiazol-3-amine;
2) 3-{1-[1-(4-methoxyphenyl)piperidin-4-yl]-4-methyl-1H-imidazo[4,5-c]pyridin-2-yl}pyrazin-2-amine; and
3) siRNA of CDK8 and/or CDK19.

(15) Regulatory T cells, which are produced by the method of any one of the above-mentioned items (8) to (14).

(16) A pharmaceutical composition for treating cancers, autoimmune diseases, inflammatory diseases, or allergic diseases, including as an active ingredient regulatory T cells produced by the method of any one of the above-mentioned items (8) to (14).

(17) A treatment method for cancers, autoimmune diseases, inflammatory diseases, or allergic diseases, including using the pharmaceutical composition of the above-mentioned item (2).

(18) A treatment method for cancers, autoimmune diseases, inflammatory diseases, or allergic diseases, including using the pharmaceutical composition of the above-mentioned item (16).

Advantageous Effects of Invention

The novel compound having CDK8 and/or CDK19 inhibitory activity of the present invention can induce Foxp3 in T cells to form Tregs in vivo, and hence can be used as a pharmaceutical composition for treating cancers, autoimmune diseases, inflammatory diseases, or allergic diseases. In addition, Foxp3 can be induced by treating T cells with the compound having CDK8 and/or CDK19 inhibitory activity in vitro, and hence the compound is expected to be applied to a Treg cell therapy and the like.

BRIEF DESCRIPTION OF DRAWINGS

In FIG. 5(b), the black line represents measured data, the red line represents a peak of non-dividing cells, and the blue line represents a peak of dividing cells. In addition, Cell Trace Violet represents the number of times of cell growth by being distributed to daughter cells through cell division ((2) of Example 7).

In FIG. 7(a), "Treg DEPLETION" represents a case in which Tregs are depleted from the body of a model mouse through diphtheria toxin administration.

In FIG. 7(a), "Treg DEPLETION" represents a case in which Tregs are depleted from the body of a model mouse through diphtheria toxin administration.

DESCRIPTION OF EMBODIMENTS

Figure 1:
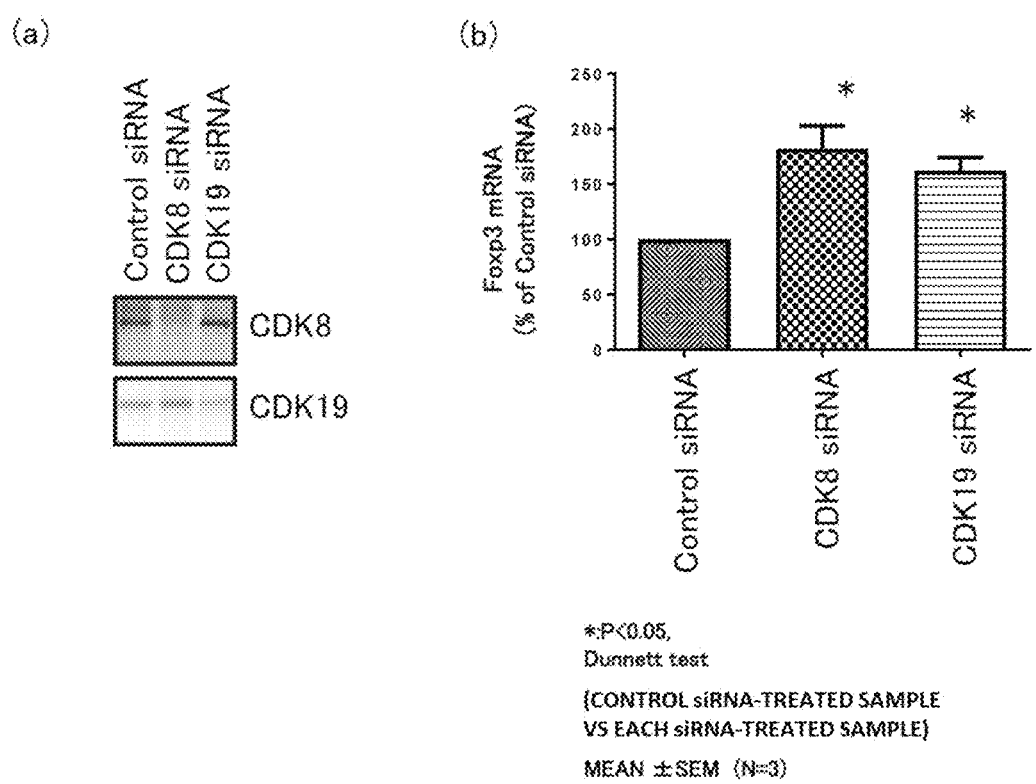
FIG. 1(a) are western blots for showing the knockdown of CDK8 and CDK19 proteins by CDK8 siRNA and CDK19 siRNA.
FIG. 1(b) is a graph for showing the amounts of Foxp3 mRNA induced when CDK8 and CDK19 proteins are knocked down by CDK8 siRNA and CDK19 siRNA, respectively (Example 3).

In the present invention, a novel compound having CDK8 and/or CDK19 inhibitory activity is 4-[1-(2-methyl-1H-benzimidazol-5-yl)-1H-imidazo[4,5-c]pyridin-2-yl]-1,2,5-oxadiazol-3-amine (hereinafter referred to as "Compound 1") or 3-{1-[1-(4-methoxyphenyl)piperidin-4-yl]-4-methyl-1H-imidazo[4,5-c]pyridin-2-yl}pyrazin-2-amine (hereinafter referred to as "Compound 2"), and may be produced by, for example, a method as shown in Synthesis Examples to be described later.

Compound 1 or Compound 2 is isolated and purified as a free compound or a salt, a hydrate, a solvate, or a polymorphic crystal substance thereof. A salt of Compound 1 or Compound 2 may also be produced by subjecting the compound to a conventional salt-forming reaction.

The isolation and the purification are performed by applying general chemical operations, such as extraction, fractional crystallization, and various types of fractional chromatography.

Various isomers may be produced by selecting appropriate starting compounds, or may be separated by utilizing differences in physicochemical properties between the isomers. For example, an optical isomer is obtained by a general optical resolution method for a racemic compound (e.g., fractional crystallization for inducing a diastereomer salt with an optically active base or acid, or chromatography using a chiral column or the like), and may also be produced from an appropriate optically active starting compound.

Compound 1 or Compound 2 also encompasses its pharmaceutically acceptable prodrug. The pharmaceutically acceptable prodrug refers to a compound having a group that may be converted into, for example, an amino group, a hydroxyl group, or a carboxyl group through solvolysis or under physiological conditions. Examples of the group forming the prodrug include groups described in Prog. Med., 5, 2157-2161 (1985) and "Pharmaceutical Research and Development" (Hirokawa-Shoten Ltd., 1990), Vol. 7 Molecular Design 163-198.

The salt of Compound 1 or Compound 2 refers to a pharmaceutically acceptable salt of the compound, and the compound may form an acid addition salt or a salt with a base depending on the kind of substituent. A specific example thereof is an acid addition salt with: an inorganic acid, such as hydrochloric acid, hydrobromic acid, hydroiodic acid, sulfuric acid, nitric acid, or phosphoric acid; or an organic acid, such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, or glutamic acid.

The present invention also encompasses various hydrates or solvates, and polymorphic crystal substances of Compound 1, Compound 2, or a salt thereof. The present invention also encompasses compounds labeled with various radioactive or non-radioactive isotopes.

The compound of the present invention can induce Foxp3 in T cells to form Tregs in vivo, and hence is applicable to various pathological immune responses, for example, cancers, autoimmune diseases (e.g., rheumatoid arthritis, systemic lupus erythematosus, type 1 diabetes, multiple sclerosis, pernicious anemia, pemphigus, and vasculitis), inflammatory diseases (e.g., ulcerative colitis and Crohn's disease), and allergic diseases.

A pharmaceutical composition for use in treating autoimmune diseases and the like containing the compound of the present invention as an active ingredient is prepared using a carrier, an excipient, and other additives that are generally used for drug formulation. The pharmaceutical composition may be administered by oral administration in the form of a tablet, a pill, a capsule, a granule, a powder, a liquid, or the like, or parenteral administration in the form of an injection, such as an intravenous injection or an intramuscular injection, a suppository, a transdermal preparation, a transnasal preparation, an inhalant, or the like.

In general, in the case of oral administration, a proper daily dose per weight is from about 0.001 mg/kg to about 100 mg/kg, preferably from 0.1 mg/kg to 30 mg/kg, more preferably from 0.1 mg/kg to 10 mg/kg, and the dose is administered in one or two to four portions. In the case of intravenous administration, a proper daily dose per weight is from about 0.0001 mg/kg to about 10 mg/kg, and the daily dose is administered in one or a plurality of portions. In addition, in the case of a transmucosal preparation, a daily dose per weight is from about 0.001 mg/kg to 100 mg/kg, and the daily dose is administered in one or a plurality of portions. The dose is appropriately determined depending on individual cases in consideration of symptoms, age, sex, and the like.

The pharmaceutical composition of the present invention contains 0.01 wt % to 100 wt %, and in a certain embodiment, 0.01 wt % to 50 wt % of one or more kinds of the compound of the present invention or the salt thereof as an active ingredient, though the content varies depending on an administration route, a dosage form, an administration site, and the kinds of excipient and additives.

As a solid composition for oral administration according to the present invention, a tablet, a powder, a granule, or the like is used. In such solid composition, one or more active substances are mixed with at least one inert excipient, such as lactose, mannitol, glucose, hydroxypropyl cellulose, microcrystalline cellulose, starch, polyvinylpyrrolidone, or magnesium aluminometasilicate. The composition may contain an inert additive, for example, a lubricant, such as magnesium stearate, or a disintegrant, such as sodium carboxymethyl starch, or a solubilizing aid in accordance with a conventional method. The tablet or the pill may be subjected to sugarcoating or gastric or enteric coating as required.

A liquid composition for oral administration includes an emulsion, a solution, a suspension, a syrup, an elixir, and the like, and contains a generally used inert solvent, for example, purified water or ethanol. The composition may contain, in addition to the inert solvent, a pharmaceutical aid, such as a solubilizer, a humectant, or a suspending agent, a sweetening agent, a taste-masking agent, a flavoring agent, and a preservative.

An injection for parenteral administration includes a sterile aqueous or non-aqueous solution, suspension, and emulsion. An aqueous solvent includes, for example, distilled water for injection and physiological saline. A non-aqueous solvent is, for example, propylene glycol, polyethylene glycol, a plant oil, such as olive oil, an alcohol, such as ethanol, or Polysorbate 80 (Japanese Pharmacopoeia name). Such composition may further contain a tonicity agent, a preservative, a humectant, an emulsifier, a dispersant, a stabilizer, and a solubilizing aid. Such composition is sterilized, for example, by filtration through a bacterial-retaining filter, blending of a microbicide, or irradiation. In addition, such composition may be used by producing a sterile solid composition, and dissolving or suspending the sterile solid composition in sterile water or a sterile injectable solvent before use.

In the present invention, Tregs can be induced in vitro by the compound of the present invention and any other compound having CDK8 and/or CDK19 inhibitory activity (hereinafter referred to as "CDK8/CDK19 inhibitor"). Accordingly, the present invention is applicable to, for example, the treatment of cancers, autoimmune diseases, inflammatory diseases, or allergic diseases based on cell therapy and the like.

Examples of the CDK8/CDK19 inhibitor to be used in the present invention include known CDK8 and/or CDK19 inhibitors, in addition to Compound 1: 4-[1-(2-methyl-1H-benzimidazol-5-yl)-1H-imidazo[4,5-c]pyridin-2-yl]-1,2,5-oxadiazol-3-amine, Compound 2: 3-{1-[1-(4-methoxyphenyl)piperidin-4-yl]-4-methyl-1H-imidazo[4,5-c]pyridin-2-yl}pyrazin-2-amine, or salts, hydrates, and solvates thereof. Specific examples thereof include compounds described in U.S. Pat. No. 8,598,344 B2, WO 2013/116786 A1, Proc. Natl. Acad. Sci. U.S.A. 109 13799-13804 (2012), WO 2013/001310 A1, WO 2013/040153 A1, WO 2014/029726

A1, WO 2014/063778 A1, WO 2014/072435 A1, WO 2014/090692 A1, WO 2014/106606 A1, WO 2014/123900 A1, WO 2014/154723 A1, WO 2014/194245 A1, WO 2015/049325 A1, WO 2015/100420 A1, WO 2015/144290 A1, WO 2015/159937 A1, WO 2015/159938 A1, and WO 2016/009076 A1.

In the present invention, the T cells to be treated with the CDK8/CDK19 inhibitor are T cells that are a kind of lymphocytes present in, for example, peripheral blood, spleen, or lymph nodes. In another embodiment, the T cells are non-regulatory T cells. The non-regulatory T cells include T cells from which regulatory T cells can be induced. In still another embodiment, the T cells are Foxp3-negative CD4$^+$ T cells (CD4$^+$ Foxp3$^-$ T cells) or CD4$^+$CD25$^-$ T cells (CD4$^+$CD25$^-$ Foxp3$^-$ T cells), or CD8$^+$ T cells (CD8$^+$ Foxp3$^-$ T cells). Examples thereof include naive T cells that have not received antigenic stimulation yet and express a CD45RA antigen on their cell surfaces (CD4$^+$ CD25$^-$ CD45RA$^+$ Foxp3$^-$ T cells). Further, naive T cells sorted by CD44, CCR7, or CD62L may also be used. Specific examples thereof include CD4$^+$CD25$^-$ CD44$^-$ CD62L$^+$ Foxp3$^-$ T cells. In addition, in the present invention, examples of the T cells to be treated with the compound having CDK8 and/or CDK19 inhibitory activity include memory T cells that have received antigenic stimulation and express a CD45RO antigen on their cell surfaces (CD4$^+$ CD25$^-$ CD45RO$^+$ Foxp3$^-$ T cells). Further, memory T cells sorted by CD44 or CD62L may also be used. Specific examples thereof include CD4$^+$ CD25$^-$ CD44$^+$ CD62L$^-$ Foxp3$^-$ effector memory T cells.

The treatment of the CD4$^+$ CD25$^-$ Foxp3$^-$ T cells only needs to be performed, for example, in the presence of 0.01 nM to 10,000 nM, preferably 0.1 nM to 1,000 nM of the CDK8/CDK19 inhibitor and a T cell receptor stimulant (TCR stimulant) under an atmosphere having a $CO_2$ concentration of from 1% to 10% or 5% at from 30° C. to 42° C. or 37° C. for from 18 hours to 240 hours or from 40 hours to 120 hours. In the present invention, it is recommended that a combination of an anti-CD3 antibody and 1 μg/mL to 100 μg/mL or 1 μg/mL to 10 μg/mL of an anti-CD28 antibody be used as the TCR stimulant. Beads coated with the anti-CD3 antibody and the anti-CD28 antibody may be used. In addition, antigen-presenting cells (APCs) and an antigen may also be used. Further, in TCR stimulation, TGF-β, rapamycin, or retinoic acid may be used in combination.

When the T cells are treated in vitro with the CDK8/CDK19 inhibitor according to the present invention, high Foxp3 induction efficiency is obtained as compared to TGF-β, which has hitherto been generally used, and a larger number of Tregs (CD4$^+$ CD25$^+$ Foxp3$^+$ T cells) can be prepared in vitro. Specifically, for example, the present invention may be utilized for cell therapy involving separating effector memory T cells from a patient, treating the effector memory T cells with the CDK8/CDK19 inhibitor under TCR stimulation to induce Foxp3 in the cells, further appropriately performing known epigenomic treatment as required, and then returning the cells to the patient, to thereby suppress the disease.

EXAMPLES

Now, the present invention is described specifically by way of Reference Examples and Examples for better understanding of the present invention. Needless to say, however, the present invention is by no means limited thereto. First, production methods for Compound 1 and Compound 2 of the present invention are shown, and further, various pharmacological tests are described in detail.

(Example 1) Production of Compound 1

In this Example, production methods for Compound 1 and its dihydrochloride (in the following Examples and Reference Examples, the dihydrochloride of Compound 1 is referred to as "Compound 1 Salt") are described. First, a production method for a starting compound for synthesizing Compound 1 is described in Production Examples 1 and 2, and a synthesis method for Compound 1 and a production method for Compound 1 Salt are described in Synthesis Examples 1 and 2. The production methods for the starting compound, Compound 1, and Compound 1 Salt are not limited to the following methods, and the compounds and the salt may be produced by methods obvious to a person skilled in the art.

In addition, in Synthesis Examples and Production Examples, the following abbreviations are used in some cases.

Dat: physicochemical data.

MASS (ESI, m/z): m/z value in ESI-MS. The value represents [M+H]$^+$ unless otherwise stated.

$^1$H NMR: δ (ppm) of peaks in 1H NMR in DMSO-d6 under room temperature.

2) Production Example 2

A mixture of 2-methyl-N-(3-nitropyridin-4-yl)-1H-benzimidazol-5-amine (14.6 g) produced in Production Example 1, ethanol (245 mL), and 10% palladium/carbon (wetted with ca. 50% water, 1.46 g) was stirred under a hydrogen atmosphere of 1 atm at room temperature for 21.5 hours. The reaction mixture was filtered through Celite, and the filtrate was concentrated under reduced pressure to afford N$^4$-(2-methyl-1H-benzimidazol-5-yl)pyridine-3,4-diamine (14.6 g). Physicochemical data on the product is shown below.
Dat: MASS (ESI, m/z) 240 [M+H]+

2) Production Example 2

A mixture of 2-methyl-N-(3-nitropyridin-4-yl)-1H-benzimidazol-5-amine (14.6 g) produced in Production Example 1, ethanol (245 mL), and 10% palladium/carbon (wetted with ca. 50% water, 1.46 g) was stirred under a hydrogen atmosphere of 1 atm at room temperature for 21.5 hours. The reaction mixture was filtered through Celite, and the filtrate was concentrated under reduced pressure to afford N$^4$-(2-methyl-1H-benzimidazol-5-yl)pyridine-3,4-diamine (14.6 g) Physicochemical data on the product is shown below.
Dat: MASS (ESI, m/z) 240 [M+H]$^+$

3) Synthesis Example 1

In this Synthesis Example, the production method for Compound 1 is shown.

[Chem. 1]

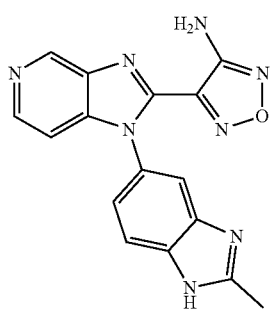

Compound 1

To a solution of 4-amino-1,2,5-oxadiazole-3-carbonitrile (9.03 g) in methanol (98.2 mL), sodium methoxide (28% methanol solution, 1.63 mL) was added, and the mixture was stirred at room temperature for 30 minutes. The reaction mixture, methanol (19.6 mL), and acetic acid (4.69 mL) were added to $N^4$-(2-methyl-1H-benzimidazol-5-yl)pyridine-3,4-diamine (11.2 g) produced in Production Example 2, and the mixture was stirred at 70° C. for 18 hours. Acetic acid (4.69 mL) was added to the reaction mixture, and the mixture was further stirred at 70° C. for 22 hours. The reaction mixture was filtered, and the filtrate was concentrated under reduced pressure. The residue was washed with methanol (100 mL) and dried by heating under reduced pressure to afford 4-[1-(2-methyl-1H-benzimidazol-5-yl)-1H-imidazo[4,5-c]pyridin-2-yl]-1,2,5-oxadiazol-3-amine (7.75 g). Physicochemical data on the product is shown below.

Dat: $^1$H NMR (400 MHz, DMSO-d6) δ 2.55 (3H, s), 6.89 (2H, s), 7.21-7.31 (2H, m), 7.56-7.78 (2H, m), 8.45 (1H, d, J=5.6 Hz), 9.23 (1H, d, J=0.9 Hz), 12.6 (1H, s).

MASS (ESI, m/z) 333 [M+H]$^+$

4) Synthesis Example 2

In this Synthesis Example, the production method for Compound 1 Salt is shown.

[chem. 2]

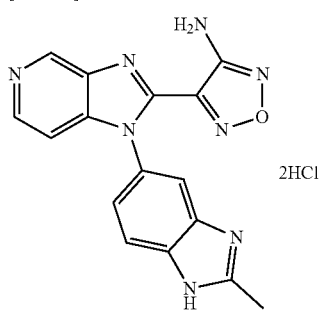

2HCl

Dihydrochloride of Compound 1

To a suspension of 4-[1-(2-methyl-1H-benzimidazol-5-yl)-1H-imidazo[4,5-c]pyridin-2-yl]-1,2,5-oxadiazol-3-amine (37.3 g) produced in Synthesis Example 1 in 1,4-dioxane (373 mL), a 4 M hydrogen chloride/1,4-dioxane solution (224 mL) was added, and the mixture was stirred at room temperature for 17 hours. Insoluble matter was collected by filtration, washed with 1,4-dioxane (149 mL), and dried by heating under reduced pressure. Diethyl ether (270 mL) was added to the resultant solid, and the mixture was stirred at room temperature for 2 hours. Insoluble matter was collected by filtration, washed with diethyl ether (90 mL), and dried by heating under reduced pressure. Ethanol (900 mL) was added to the resultant solid, and the mixture was stirred at 90° C. for 1 hour, then allowed to cool to room temperature, and stirred at the temperature for 14 hours. Insoluble matter was collected by filtration, washed with ethanol (100 mL), and dried by heating under reduced pressure. Ethyl ether (435 mL) was added to the resultant solid, and the mixture was stirred at 50° C. for 6 hours. Insoluble matter was collected by filtration at the temperature, and washed with diethyl ether (44 mL). The resultant was dried by heating under reduced pressure to afford 4-[1-(2-methyl-1H-benzimidazol-5-yl)-1H-imidazo[4,5-c]pyridin-2-yl]-1,2,5-oxadiazol-3-amine dihydrochloride (42.0 g). Physicochemical data on the product is shown below.

Dat: $^1$H NMR (400 MHz, DMSO-d6) δ 2.86 (3H, s), 6.97 (2H, s), 7.74-7.83 (2H, m), 8.00-8.06 (1H, m), 8.22-8.26 (1H, m), 8.73 (1H, d, J=6.5 Hz), 9.71 (1H, s).

MASS (ESI, m/z) 333 [M+H]$^+$

(Example 2) Production of Compound 2

In this Example, the production method for Compound 2 is described. First, a production method for a starting compound for synthesizing Compound 2 is described in Production Examples 3 to 5, and a synthesis method for Compound 2 is described in Synthesis Example 3. The production methods for the starting compound and Compound 2 are not limited to the following methods, and the compounds may be produced by methods obvious to a person skilled in the art.

1) Production Example 3

To a solution of 4-chloro-2-methyl-3-nitropyridine (7 g) and 1-(4-methoxyphenyl)piperidin-4-amine (11 g) in N-methyl-2-pyrrolidone (70 mL), N,N-diisopropylethylamine (21 mL) was added, and the mixture was stirred at 140° C. for 2 hours. The mixture was allowed to cool to room temperature, and a saturated aqueous solution of sodium bicarbonate and water were added to the reaction mixture, followed by extraction with ethyl acetate. The organic layer was washed with water and a saturated aqueous solution of sodium chloride, and dried over anhydrous magnesium sulfate. After that, the solvent was removed by evaporation under reduced pressure. Ethyl acetate (50 mL) and hexane (200 mL) were added to the residue, and insoluble matter was collected by filtration. The resultant was dried under reduced pressure to afford N-[1-(4-methoxyphenyl)piperidin-4-yl]-2-methyl-3-nitropyridin-4-amine (11.4 g). Physicochemical data on the product is shown below.

Dat: MASS (ESI, m/z) 343 [M+H]$^+$

2) Production Example 4

A mixture of N-[1-(4-methoxyphenyl)piperidin-4-yl]-2-methyl-3-nitropyridin-4-amine (11.4 g) produced in Production Example 3, ethyl acetate (150 mL), methanol (150 mL), and 10% palladium/carbon (wetted with ca. 50% water, 3.54 g) was stirred under a hydrogen atmosphere of 1 atm at room temperature for 16 hours. The reaction mixture was filtered through Celite, and the filtrate was concentrated under reduced pressure. Ethyl acetate was added to the residue, and the mixture was stirred. After that, insoluble matter was collected by filtration. The resultant was dried under reduced pressure to afford $N^4$-[1-(4-methoxyphenyl)piperidin-4-yl]-2-methylpyridine-3,4-diamine (10.3 g). Physicochemical data on the product is shown below.

Dat: MASS (ESI, m/z) 313 [M+H]$^+$

3) Production Example 5

A mixture of $N^4$-[1-(4-methoxyphenyl)piperidin-4-yl]-2-methylpyridine-3,4-diamine (5.17 g) produced in Production Example 4, 3-aminopyrazine-2-carboxylic acid (2.42 g), N,N-diisopropylethylamine (8 mL), O-(7-azabenzotriazol-1-yl)-N,N,N',N'-tetramethyluronium hexafluorophosphate (6.5 g), and dichloromethane (75 mL) was stirred at room temperature overnight. 3-Aminopyrazine-2-carboxylic acid (350 mg), N,N-diisopropylethylamine (850 µL), and O-(7-azabenzotriazol-1-yl)-N,N,N',N'-tetramethyluronium hexafluorophosphate (950 mg) were added to the reaction mixture, and the mixture was stirred at room temperature for 5 hours. A saturated aqueous solution of sodium bicarbonate was added to the reaction mixture, followed by extraction with chloroform. The organic layer was washed with a saturated aqueous solution of sodium chloride, and the solvent was removed by evaporation under reduced pressure. The residue was purified by silica gel column chromatography to afford 3-amino-N-(4-{[1-(4-methoxyphenyl)piperidin-4-yl]amino}-2-methylpyridin-3-yl)pyrazine-2-carboxamide (7.45 g).

Physicochemical data on the product is shown below.
Dat: MASS (ESI, m/z) 434 [M+H]$^+$ 4) Synthesis Example 3

In this Synthesis Example, the production method for Compound 2 is shown.

[Chem. 3]

Compound 2

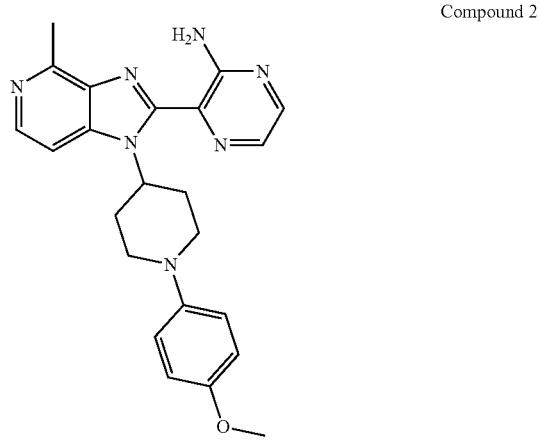

A mixture of 3-amino-N-(4-{[1-(4-methoxyphenyl)piperidin-4-yl]amino}-2-methylpyridin-3-yl)pyrazine-2-carboxamide (7.45 g) produced in Production Example 5, potassium carbonate (7.07 g), and ethanol (75 mL) was stirred using a microwave reactor at 150° C. for 7 hours. The reaction was performed in four batches. The reaction mixture was allowed to cool to room temperature, and a saturated aqueous solution of ammonium chloride was added thereto, followed by extraction with chloroform. The organic layer was washed with a saturated aqueous solution of sodium chloride, and the solvent was removed by evaporation under reduced pressure. The residue was purified by silica gel column chromatography to afford 3-{1-[1-(4-methoxyphenyl)piperidin-4-yl]-4-methyl-1H-imidazo[4,5-c]pyridin-2-yl}pyrazin-2-amine (5.67 g). Physicochemical data on the product is shown below.

Dat: $^1$H NMR (500 MHz, DMSO-d6) δ 1.98-2.06 (2H, m), 2.51-2.62 (2H, m), 2.70-2.78 (2H, m), 2.77 (3H, s), 3.68-3.73 (2H, m), 3.71 (3H, s), 5.49-5.58 (1H, m), 6.83-6.87 (2H, m), 6.96-7.00 (2H, m), 7.59 (1H, d, J=5.7 Hz), 7.67 (2H, s), 7.97 (1H, d, J=2.4 Hz), 8.16 (1H, d, J=2.4 Hz), 8.21 (1H, d, J=5.7 Hz).

MASS (ESI, m/z) 416 [M+H]$^+$ (Example 3) Correlations Between CDK8 and CDK19, and Foxp3 mRNA Induction In this Example, correlations between CDK8 and CDK19, and Foxp3 mRNA induction in mouse spleen cells were confirmed. Spleen cells derived from 9- to 11-week-old C57BL/6 mice (manufactured by SLC) were disrupted on a nylon mesh and filtered to prepare a cell suspension. Further, CD4$^+$ T cells were prepared from the cell suspension using CD4 Microbeads, Mouse (manufactured by Miltenyi Biotec). The prepared cells were transfected with 250 nM of Negative Control siRNA (manufactured by Thermo Fisher Scientific), CDK8 siRNA (s113914; manufactured by Thermo Fisher Scientific), or CDK19 siRNA (s95476; manufactured by Thermo Fisher Scientific) using GenomONE-si (manufactured by Ishihara Sangyo Kaisha, Ltd.), stimulated with an anti-CD3 antibody (145-2C11, ATCC CRL-1975; Proc. Natl. Acad. Sci. USA vol. 84 (1987), p1374-1378) and an anti-CD28 antibody (37.51; manufactured by BD), and cultured under a 5% CO$_2$ atmosphere at 37° C. After 2 days, the cells were transfected again with CDK8 siRNA or CDK19 siRNA, and cultured under a 5% CO$_2$ atmosphere at 37° C. After 1 day, the cells were subjected to Foxp3 induction treatment by culture in the presence of 3.3×10$^6$ beads/mL of Gibco Dynabeads Mouse T-Activator CD3/28 (manufactured by Thermo Fisher Scientific), 250 U/mL of mIL-2 (manufactured by R&D), and 5 ng/mL of hTGF-131 (manufactured by Peprotech) under a 5% CO$_2$ atmosphere at 37° C. After 1 day from the treatment, total RNA was extracted from the T cells, cDNA was synthesized, and the expression amount of Foxp3 mRNA and the expression amount of 18s rRNA mRNA were measured by Taqman assay (Foxp3: Mm00475162 m1, 18S: Mm03928990 gl; manufactured by Thermo Fisher Scientific). After that, the Foxp3 mRNA expression value was corrected with the 18S rRNA expression value. Further, a percent value to the Negative Control siRNA-treated sample was determined. The results of three trials are shown in FIG. 1(b). Foxp3 mRNA was induced by the knockdown of CDK8 or CDK19, revealing that Foxp3 was induced in T cells by suppressing the function of CDK8 or CDK19.

Under the above-mentioned conditions, through use of the T cells subjected to the Foxp3 induction treatment on day 3, a validity for knockdown conditions for CDK8 and CDK19 proteins by CDK8 siRNA or CDK19 siRNA was confirmed by western blotting using an anti-CDK8 antibody (manufactured by Cell Signaling Technology) and an anti-CDK19 antibody (manufactured by SIGMA). As shown in FIG. 1(a), it was confirmed that the above-mentioned conditions were valid as the knockdown conditions for CDK8 and CDK19 proteins by CDK8 siRNA or CDK19 siRNA.

(Example 4) CDK8/19 Inhibitory Activities of Compound 1 Salt and Compound 2

In this Example, CDK8 and CDK19 inhibitory activities were confirmed for Compound 1 Salt produced in Example 1 and Compound 2 produced in Example 2. QSS Assist™ CDK8/CycC_ELISA kit (manufactured by Carna Biosciences) was used for the kinase activity measurement of CDK8. An enzyme solution (10 µL) and an ATP/Substrate/Metal solution (5 µL) each included with the kit, and a compound solution (prepared with an assay buffer included with the kit so as to have a 4-fold concentration with respect to a final concentration at the time of reaction, 5 µL) were added to a plate coated with streptavidin (manufactured by Thermofisher Scientific), followed by incubation at room temperature for 90 minutes. After washing with a wash buffer (50 mM Tris-HCl (pH 7.5), 150 mM NaCl, 0.02% Tween-20), 100 µL of a 0.1% BSA solution was added to the plate, followed by incubation at room temperature for 30 minutes. The 0.1% BSA solution was removed, and then 50 µL of a primary antibody solution included with the kit was added to the plate, followed by incubation at room temperature for 30 minutes. After washing with a wash buffer, 50 µL of a secondary antibody solution included with the kit was added to the plate, followed by incubation at room temperature for 30 minutes. After washing with a wash buffer, 50 µL of TMB Chromogen Solution (manufactured by Lifetechnologies) was added to the plate, followed by incubation at room temperature for 5 minutes. 50 µL of 0.1 M $H_2SO_4$ was added to the plate to stop a chromogenic reaction. Through use of measured values for OD450 and OD540, geometric averages of $IC_{50}$ values were calculated based on data obtained from four trials and three trials, respectively, for Compound 1 Salt and Compound 2. In addition, QSS Assist™ CDC2L6/CycC_ELISA kit (manufactured by Carna Biosciences) was used for the kinase activity measurement of CDK19. An enzyme solution (10 µL) and an ATP/Substrate/Metal solution (5 µL) each included with the kit, and a compound solution (prepared with an assay buffer included with the kit so as to have a 4-fold concentration with respect to a final concentration at the time of reaction, 5 µL) were added to a plate coated with streptavidin (manufactured by Thermofisher Scientific), followed by incubation at room temperature for 90 minutes. After washing with a wash buffer, 100 µL of a 0.1% BSA solution was added to the plate, followed by incubation at room temperature for 30 minutes. The 0.1% BSA solution was removed, and then 50 µL of a primary antibody solution included with the kit was added to the plate, followed by incubation at room temperature for 30 minutes. After washing with a wash buffer, 50 µL of a secondary antibody solution included with the kit was added to the plate, followed by incubation at room temperature for 30 minutes. After washing with a wash buffer, 50 µL of TMB Chromogen Solution (manufactured by Lifetechnologies) was added to the plate, followed by incubation at room temperature for 5 minutes. 50 µL of 0.1 M $H_2SO_4$ was added to the plate to stop a chromogenic reaction. Through use of measured values for OD450 and OD540, geometric averages of $IC_{50}$ values were calculated based on data obtained from three trials for both of Compound 1 Salt and Compound 2. The results are shown in Table 1. Table 1 revealed that Compound 1 Salt and Compound 2 were dual inhibitors for CDK8 and CDK19.

TABLE 1

| | | Compound 1 Salt | Compound 2 |
|---|---|---|---|
| Inhibitory activity $IC_{50}$ (nM) | CDK8 | 0.6 | 0.7 |
| | CDK19 | 4.3 | 1.9 |

(Example 5) In Vitro Induction of Foxp3 by Compound 1 Salt

In this Example, an ability to induce Foxp3 in naive cells was confirmed for Compound 1 Salt produced in Example 1.

The lymph nodes of 6- to 8-week-old Foxp3-GFP fusion protein KI mice (eFox mice) were collected, and the tissue was disrupted using ground glass, and filtered through a nylon mesh to prepare a total lymphocytic cell suspension. The eFox mice were generated in accordance with a method described in Science. 2014 Oct. 17; 346(6207): 363-8. doi: 10.1126/science.1259077. The prepared total lymphocytic cells were stained with an anti-CD4 antibody (RM-4.5; manufactured by BD), an anti-CD62L antibody (MEL-14; manufactured by BD), and an anti-CD44 antibody (IM7; manufactured by BD), and $CD4^+$ $CD25^-$ $Foxp3^-$ $CD62L^+$ $CD44^-$ naive T cells were prepared using FACSAria™ II (manufactured by BD).

Figure 2:
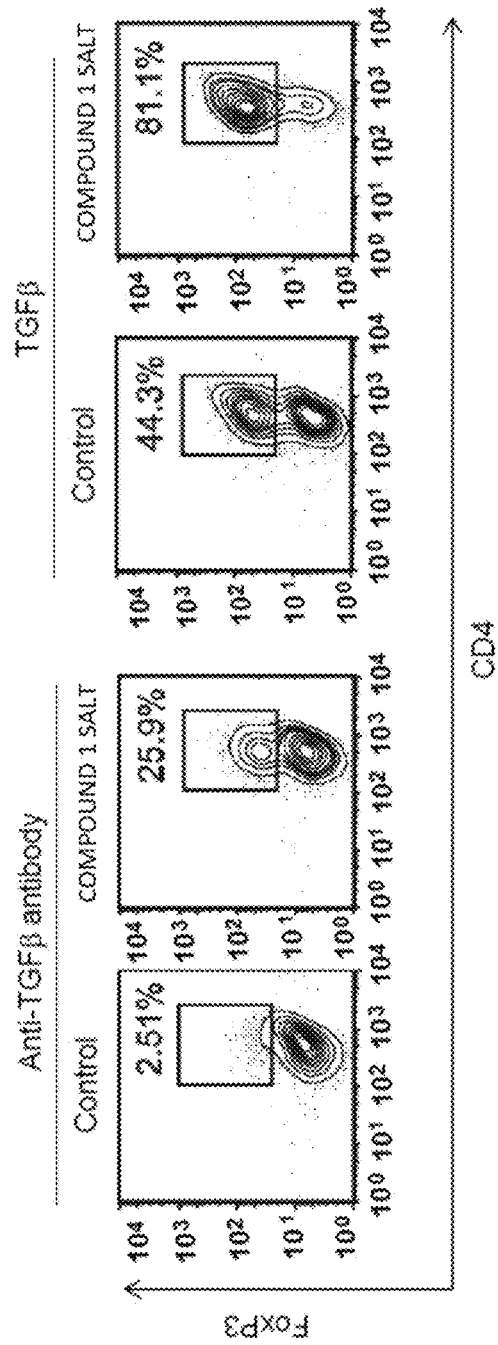
FIG. 2(a) are FACS analysis plots for showing the amounts of Foxp3 induced in naive T cells by a dihydrochloride of Compound 1 (shown as "COMPOUND 1 SALT" in FIG. 2(a), the same applies hereinafter). The results of analysis in the case of adding an anti-TGF-β antibody are shown in the left of FIG. 2(a), and the results of analysis in the case of adding TGF-β are shown in the right of FIG. 2(a).
FIG. 2(b) is a graph for showing the amounts of Foxp3 obtained by the FACS analysis of FIG. 2(a) (Example 5).
Figure 2:
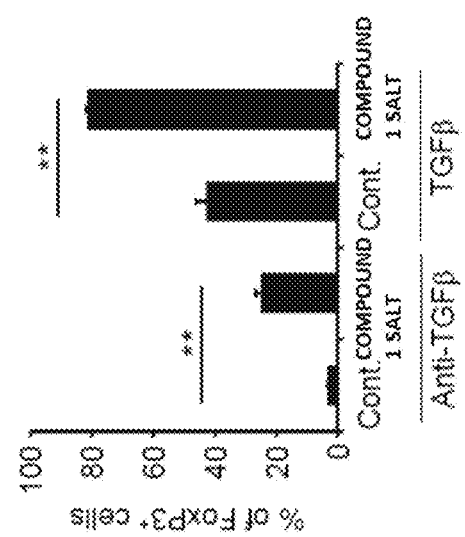

As shown in the following items (i) to (iv), the prepared naive T cells ($2\times10^5$ cells) were stimulated using 5 µL of an anti-CD3/CD28 antibody (Gibco Dynabeads Mouse T-Activator CD3/CD28; manufactured by Thermo Fisher Scientific) in the presence/absence of 2 ng/mL of hTGF-β1 (manufactured by R&D) or 10 µg/mL of an anti-TGF-β antibody (manufactured by R&D) and 1 µM of Compound 1 Salt, and treated under a 5% $CO_2$ atmosphere at 37° C. for 72 hours.
(i) Anti-TGF-β antibody (control)
(ii) Anti-TGF-β antibody+Compound 1 Salt
(iii) hTGF-β1 (control)
(iv) hTGF-β1+Compound 1 Salt The cells after the treatment were stained with an anti-CD4 antibody (manufactured by BD), and a proportion of Foxp3-GFP-positive cells was analyzed by a flow cytometry method. The results are shown in FIG. 2(a). In addition, the number (%) of those Foxp3-GFP-positive cells is shown in FIG. 2(b).

The results of FIG. 2(a) and FIG. 2(b) revealed that even under such a condition that TGF-β was blocked by the addition of the anti-TGF-β antibody, Foxp3 was significantly induced in the naive T cells by Compound 1 Salt alone (control: 2.51%, Compound 1 Salt treatment: 25.9%). The results also revealed that Foxp3 was synergistically induced in the naive T cells by using Compound 1 Salt and TGF-β in combination (TGF-β: 44.3%, TGF-β+Compound 1 treatment: 81.1%).

(Example 6) Antigen-Specific Foxp3 Induction by Compound 1 Salt

In this Example, an ability to induce Foxp3 in naive cells in an antigen-specific manner was confirmed for Compound 1 Salt produced in Example 1.

$CD4^+$ $CD25^-$ $Foxp3^-$ $CD62L^+$ $CD44^-$ naive T cells were prepared from 6- to 10-week-old DO11.10/eFox mice in the same manner as in Example 5. The DO11.10/eFox mice were generated by crossing DO11.10 mice with eFox mice. In addition, total lymph node cells were separated from 6- to 10-week-old BALB/c mice (manufactured by SLC), and stained with an anti-CD11c antibody (HL3; manufactured by BD) to prepare antigen-presenting cells (CD11c-positive cells).

Figure 3:
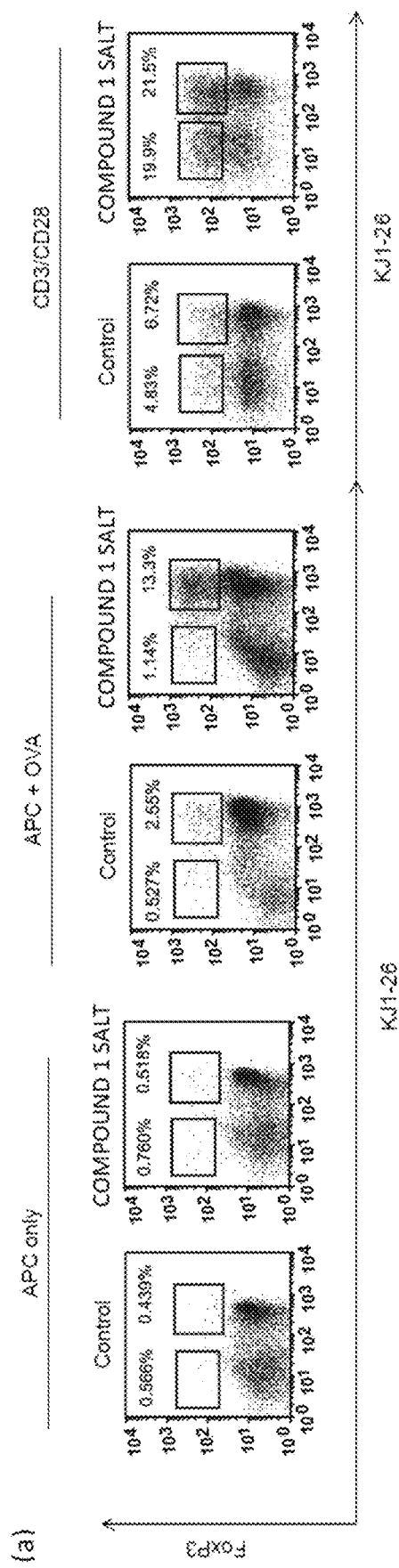
FIG. 3(a) are FACS analysis plots for showing the amounts of Foxp3 induced in naive T cells by Compound 1 Salt. A case in which only antigen-presenting cells (APCs) are present is shown in the left of FIG. 3(a), a case in which the antigen-presenting cells and an antigen (OVA) are present is shown in the center of FIG. 3(a), and a case in which a T cell receptor stimulant (CD3/CD28) is present is shown in the right of FIG. 3(a).
FIG. 3(b) are graphs for showing the amounts of Foxp3 obtained by the FACS analysis of FIG. 3(a) (Example 6).
Figure 3:
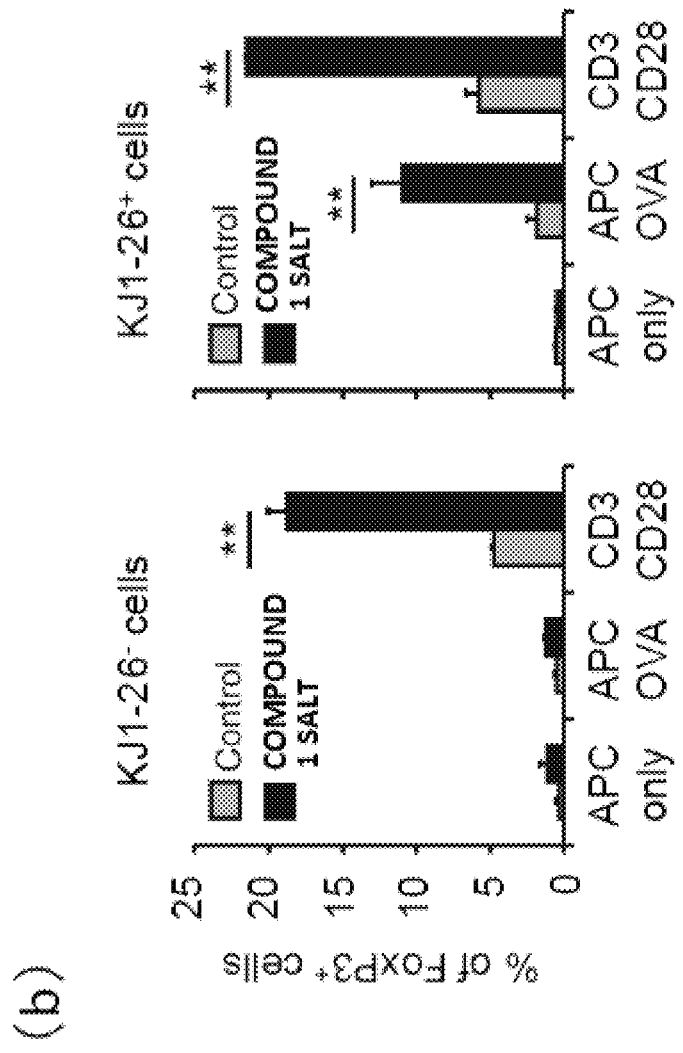

As shown in the following items (i) to (vi), the prepared naive T cells ($1 \times 10^5$ cells) were treated in the presence/absence of $2 \times 10^4$ antigen-presenting cells (APCs), 5 µM of OVA (ovalbumin peptide, $OVA_{323-339}$; manufactured by MLB), or 5 µL of an anti-CD3/CD28 antibody (Gibco Dynabeads Mouse T-Activator CD3/CD28; manufactured by Thermo Fisher Scientific) and 1 µM of Compound 1 Salt under a 5% $CO_2$ atmosphere at 37° C. for 72 hours.
(i) APC (control)
(ii) APC+Compound 1 Salt
(iii) APC+OVA (control)
(iv) APC+OVA+Compound 1 Salt
(v) Anti-CD3/CD28 antibody (control)
(vi) Anti-CD3/CD28 antibody+Compound 1 Salt The cells after each treatment were stained with an anti-DO11.10 antibody (KJ1-26, manufactured by BD), and a proportion of Foxp3-GFP-positive cells and expression of DO11.10 TCR were analyzed by a flow cytometry method. The results are shown in FIG. 3(a). In addition, the number (%) of those Foxp3-KJ1-26-positive cells is shown in FIG. 3(b).

From the results of FIG. 3(a) and FIG. 3(b), only when the naive T cells were co-stimulated with the APCs and OVA, $Foxp3^+$ T cells expressing DO11.10 TCR, which was recognized by KJ1-26, were increased by Compound 1 Salt (APC+OVA+Compound 1 Salt: 13.3%). Meanwhile, when the cells were stimulated with the anti-CD3 antibody and the anti-CD28 antibody, $Foxp3^+$ T cells not expressing DO11.10 TCR were also increased (CD3+CD28+Compound 1 Salt: 19.9%). Those results revealed that Compound 1 Salt induced $Foxp3^+$ T cells in an antigen (OVA)-specific manner.

(Example 7) Influences of Compound 1 Salt on Foxp3 Induction and Cell Growth

In this Example, Foxp3 induction in effector memory T cells and a cell growth-suppressing action of Tregs induced from the effector memory T cells were confirmed for Compound 1 Salt produced in Example 1.

(1) Foxp3 Induction in Effector Memory T Cells

Figure 4:
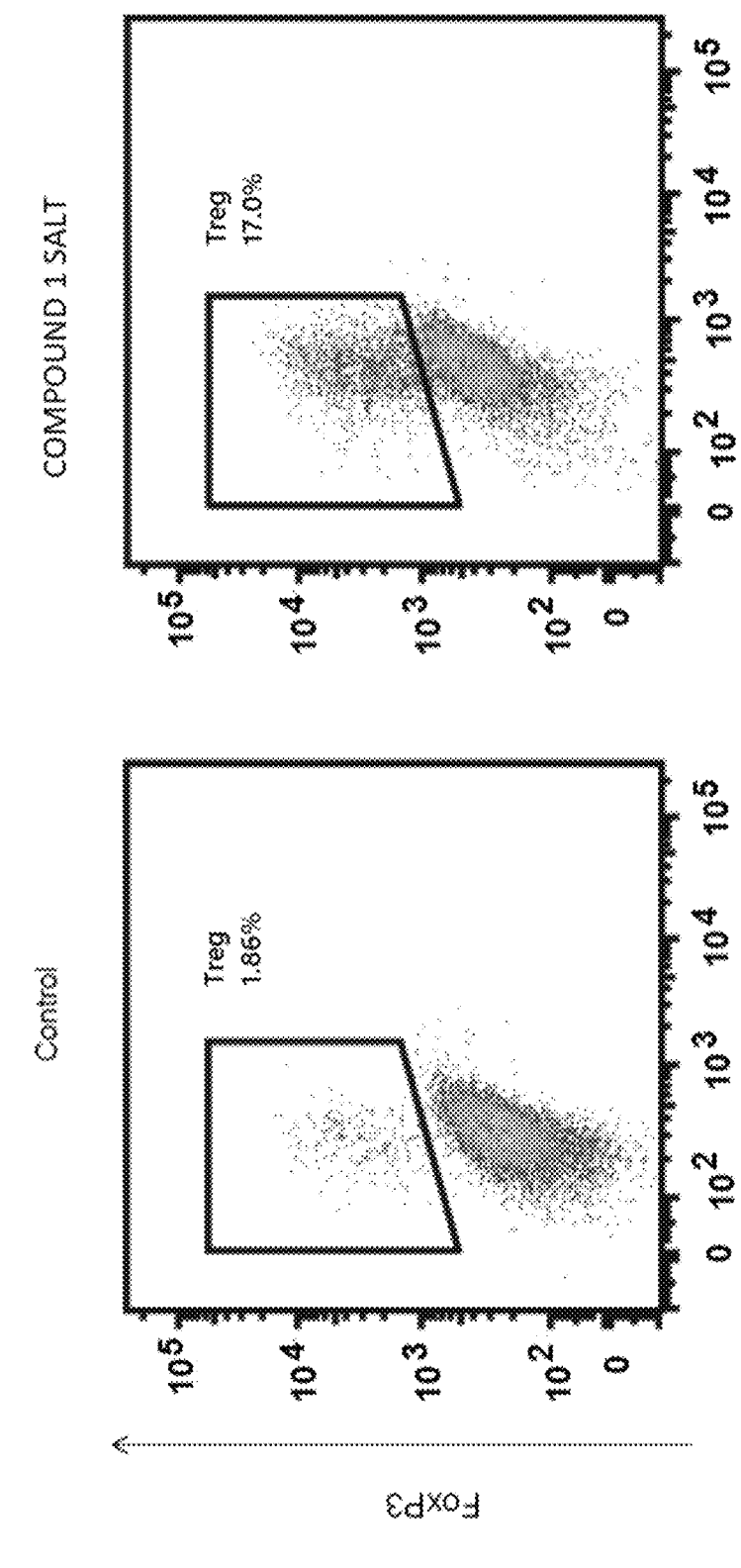
FIG. 4 are FACS analysis plots for showing the amount of Foxp3 induced in effector memory T cells by Compound 1 Salt ((1) of Example 7).

A total lymphocytic cell suspension was prepared from eFox mice in the same manner as in Example 5. The prepared total lymphocytic cells were stained with an anti-CD4 antibody (RM-4.5; manufactured by BD), an anti-CD62L antibody (MEL-14; manufactured by BD), and an anti-CD44 antibody (IM7; manufactured by BD), and effector memory T cells ($CD4^+$ $Foxp3^-$ $CD25^-$ $CD44^{hi}$ $CD62L^-$) were prepared using FACSAria™ II (manufactured by BD). The resultant effector memory T cells ($2 \times 10^5$ cells) were stimulated using 5 µL of an anti-CD3/CD28 antibody (Gibco Dynabeads Mouse T-Activator CD3/CD28; manufactured by Thermo Fisher Scientific) in the presence of hTGF-β1 (5 ng/mL) and Compound 1 Salt (1 µM), and treated under a 5% $CO_2$ atmosphere at 37° C. for 72 hours. A proportion of Foxp3-GFP-positive cells after the treatment was analyzed by a flow cytometry method. The results are shown in FIG. 4. A system free of Compound 1 Salt was used as a control. The results revealed that Foxp3 was significantly induced in the case of the treatment with Compound 1 Salt as compared to the control (control: 1.86%, Compound 1 Salt: 17.0%).

(2) Cell Growth Suppression by Tregs Induced from Effector Memory T Cells

Figure 5:
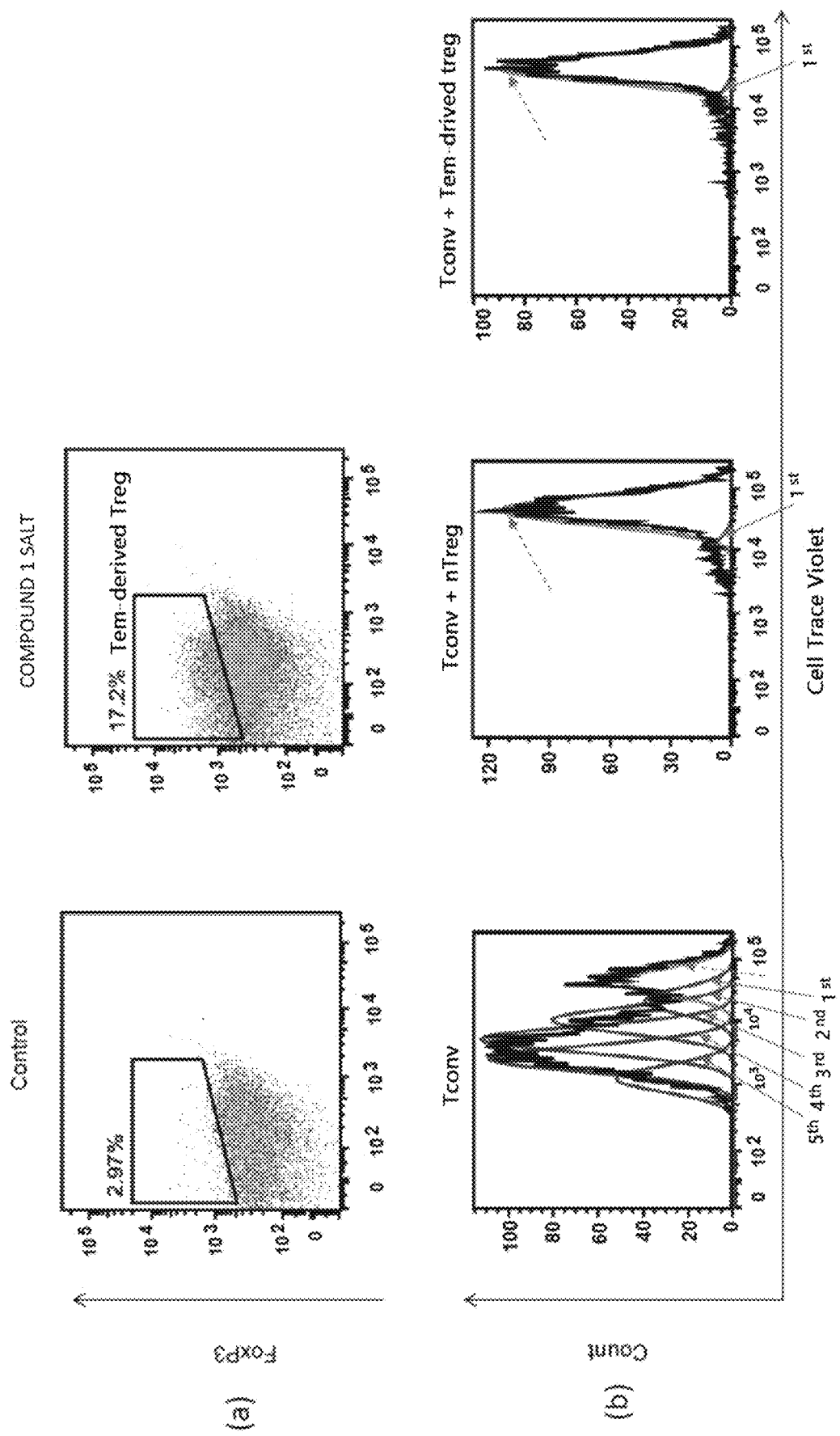
FIG. 5(a) are FACS analysis plots for showing the amount of Foxp3 induced in effector memory T cells by Compound 1 Salt.
FIG. 5(b) are graphs for showing comparison between T cell growth-suppressing actions of natural-occurring Tregs (nTregs) and regulatory T cells induced by Compound 1 Salt (Tem-derived Tregs). A T cell growth-suppressing action in the case of using a control (Tconvs) is shown in the left of FIG. 5(b), a T cell growth-suppressing action in the case of using the Tconvs and the nTregs in combination is shown in the center of FIG. 5(b), and a T cell growth-suppressing action in the case of using the Tconvs and the Tem-derived Tregs in combination is shown in the right of FIG. 5(b).

Effector memory T cells ($2 \times 10^5$ cells) prepared in the same manner as in the section (1) were treated in the presence of 5 ng/mL of hTGF-β1 and 1 µM of Compound 1 Salt. The results are shown in FIG. 5(a). A system free of Compound 1 Salt was used as a control.

The results revealed that $CD4^+$ $CD25^+$ $Foxp3^+$ regulatory T cells (Tem-derived Tregs) were significantly induced (17.2%) in the case of the treatment with Compound 1 Salt as compared to the control (2.97%).

Next, T cell growth-suppressing actions of the Tem-derived Tregs and natural-occurring Tregs (nTregs) were compared to each other. nTregs prepared from eFox mice by the same technique as that of Example 5 were used as the nTregs. In addition, naive T cells (Tconvs) prepared from BALB/c mice by the same method as that of Example 5 were used as T cells. The Tconvs were labeled with a division labeling dye Cell Tracer Violet (manufactured by Thermo Fisher Scientific). Cells containing the Tconvs and the nTregs at a ratio of 2:1 ($6 \times 10^4$ cells) or cells containing the Tconvs and the Tem-derived Tregs at a ratio of 10:1 ($4.4 \times 10^4$ cells) were cultured in the presence of antigen-presenting cells ($4 \times 10^4$ cells) and 1 µg/mL of an anti-CD3 antibody under a 5% $CO_2$ atmosphere at 37° C. for 72 hours. After that, the division labeling dye was measured with FACSAria™ II (manufactured by BD) to examine the growth state of the Tconv cells. The Tconvs ($4 \times 10^4$ cells) alone were used as a control.

The results are shown in FIG. 5(b). In FIG. 5(b), the black line represents measured data, the red line (indicated by the broken arrow in FIG. 5(b)) represents a peak of non-dividing cells, and the blue line (indicated by the solid arrow in FIG. 5(b)) represents a peak of dividing cells. The results of FIG. 5(b) revealed that in the system (control) in which none of the nTregs and the Tem-derived Tregs were added to the Tconvs, the attenuation of the division labeling dye in the Tconvs was found and five times of cell division was observed (blue line: indicated by the $1^{st}$ to $5^{th}$ arrows in the left of FIG. 5(b)), and hence the Tconv cells grew. In contrast, it was revealed that in both Tconvs+nTregs (2:1) and Tconvs+Tem-derived Tregs (10:1), the growth of the Tconv cells was suppressed at substantially the same level. This revealed that the Tem-derived Tregs had a T cell growth-suppressing effect comparable to that of the nTregs in an amount corresponding to ⅕ of that of the nTregs.

(Example 8) In Vivo Foxp3 Induction

Six- to ten-week-old DO11.10/RAG2 KO/eFox mice were immunized with a mixed emulsion of OVA ($OVA_{323-339}$; manufactured by MLB) and complete Freund's adjuvant (CFA; manufactured by BD) (100 µg OVA/mouse), and orally administered Compound 1 Salt (30 mg/kg in terms of free form) for 1 week from the day of the immunization. A system in which Compound 1 Salt was not administered was used as a control. In addition, a non-immunized system (Non Immunization) was also similarly investigated. The DO11.10/RAG2 KO/eFox mice were generated by crossing the DO11.10/eFox mice of Example 6 with RAG2 KO mice.

Figure 6:
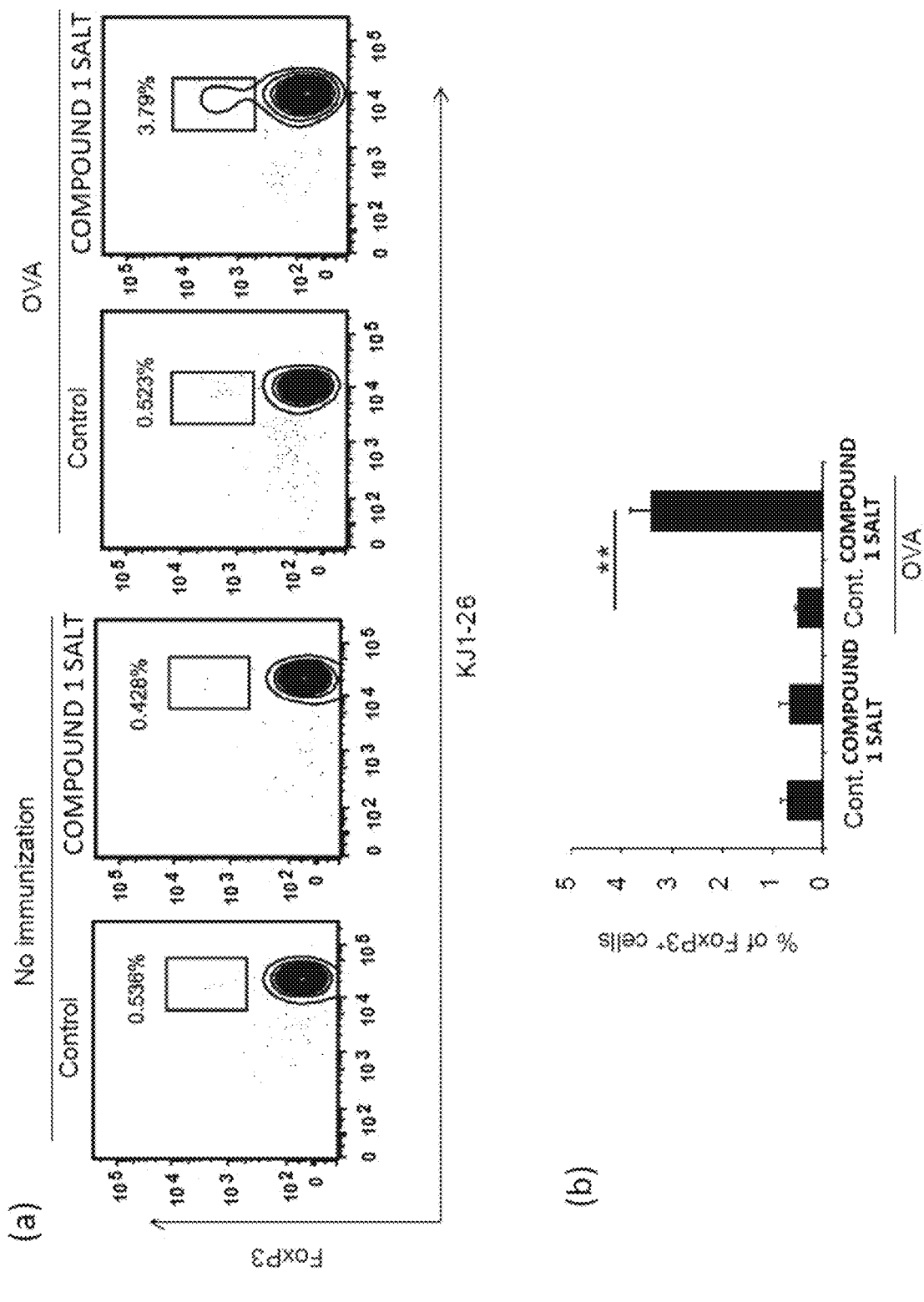
FIG. 6(a) are FACS analysis plots for showing the amounts of Foxp3 induced in lymphocytic cells from mice administered Compound 1 Salt. The amount of Foxp3 induced in the case of administering no antigen to the mice is shown in the left of FIG. 6(a), and the amount of Foxp3 induced in the case of administering an antigen (OVA) to the mice is shown in the right of FIG. 6(a).
FIG. 6(b) is a graph for showing the amounts of Foxp3 obtained by the FACS analysis of FIG. 6(a) (Example 8).

After the oral administration for 1 week, lymphocytes were collected from the mice to prepare a cell suspension by the same technique as that of Example 5. Next, the lymphocytic cells were stained with an anti-CD4 antibody (manufactured by BD) and an anti-DO11.10 antibody (manufactured by BD), and a proportion of Foxp3-GFP-positive cells was analyzed by a flow cytometry method. The results are shown in FIG. 6(a). In addition, the number (%) of those Foxp3-GFP-positive cells is shown in FIG. 6(b).

The results of FIG. 6(a) and FIG. 6(b) revealed that Foxp3-positive T cells were induced by Compound 1 Salt only in the mice administered OVA (3.79%).

(Example 9) Therapeutic Effect of Compound 1 Salt on Contact Hypersensitivity (CHS)

In this Example, a therapeutic effect of Compound 1 Salt on contact hypersensitivity in a dinitrofluorobenzene (DNFB)-induced CHS model was confirmed. The DNFB-induced CHS model was generated by the following method. 100 µL of DNFB ((0.5% (w/v) DNFB in acetone/olive oil (4/1)) was applied to the abdomen of 6- to 10-week-old Foxp3-DTR-GFP KImice (FDGmice) (Nat. Immunol. 2007 February; 8(2): 191-7) twice at an interval of 1 week to sensitize the mice. After 1 week, 20 µL of DNFB was further applied to the ear to induce DNFB-induced contact hypersensitivity (CHS). Thus, CHS model mice were generated.

Figure 7:
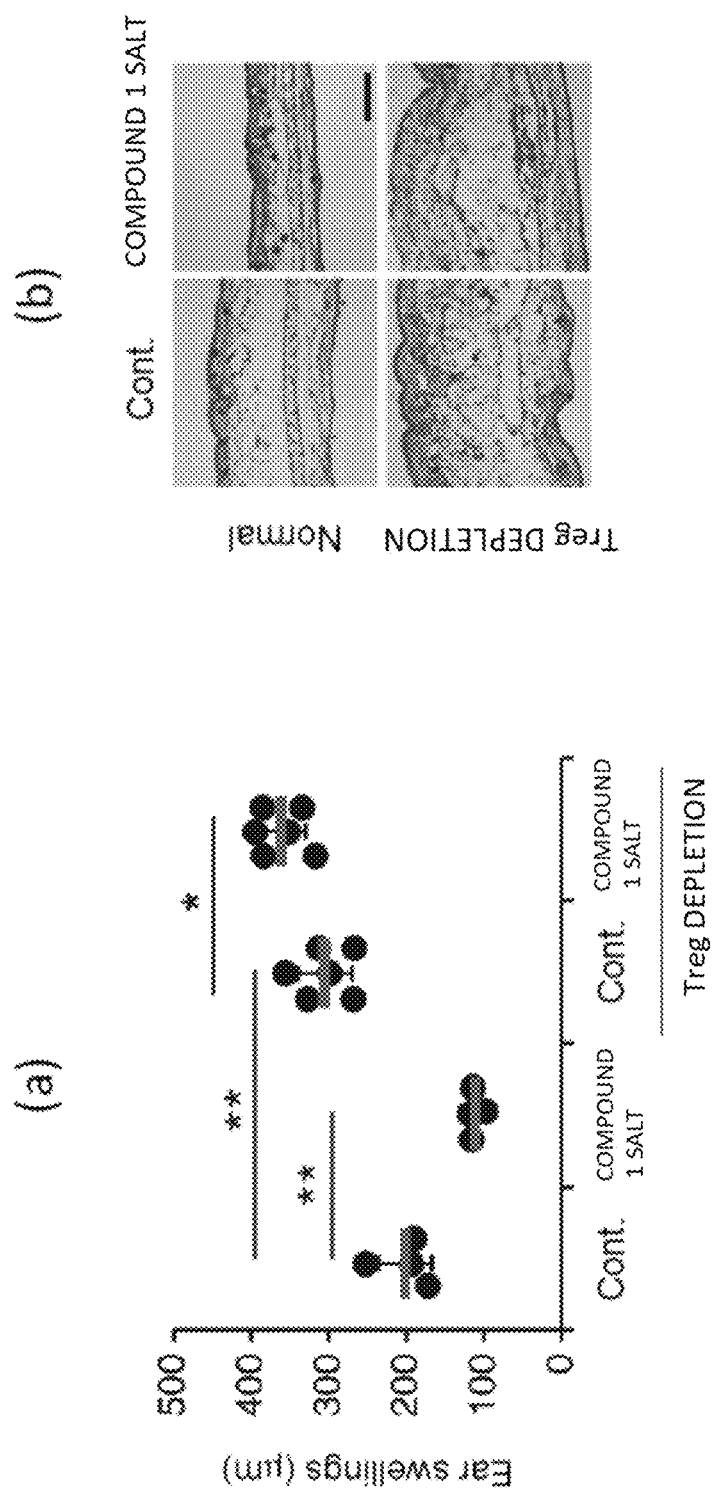
FIG. 7(a) is a graph for showing a suppressing action of Compound 1 Salt on the ear swelling of a DNFB-induced CHS model.
FIG. 7(b) are stained photographs of ear tissues of the mice of FIG. 7(a) (Example 9).

The CHS model mice were orally administered Compound 1 Salt (30 mg/kg in terms of free form) for 14 days (normal case). In addition, the CHS model mice intraperitoneally administered 50 ng of diphtheria toxin in advance were also similarly orally administered Compound 1 Salt (in the case of Treg depletion). Those CHS model mice were each bred for 14 days, and then an ear swelling was measured with a dial thickness gauge (Peacock). The results are shown in FIG. 7(a). In addition, the ear tissues of the respective mice were subjected to hematoxylin-eosin staining. The results are shown in FIG. 7(b).

The results of FIG. 7(a) and FIG. 7(b) revealed that the administration of Compound 1 Salt reduced the ear swelling of the CHS model mice. In addition, the results of the staining of the ear tissues also showed similar results. Meanwhile, when the mice were subjected to the Treg depletion treatment involving diphtheria toxin administration, the ear swelling of the mice was not reduced even by administering Compound 1 Salt. The results of the staining of the ear tissues also showed similar results. Those results revealed that the therapeutic effect of Compound 1 Salt on CHS was Treg-dependent.

(Example 10) Therapeutic Effect of Compound 1 Salt on Multiple Sclerosis

In this Example, a therapeutic effect of Compound 1 Salt in experimental autoimmune encephalomyelitis (EAE) model mice serving as a multiple sclerosis model was confirmed. The EAE model was generated by the following method. An emulsion produced by mixing equal amounts of myelin oligodendrocyte glycoprotein (MOG) peptide $MOG_{35-55}$ and complete Freund's adjuvant (CFA; manufactured by BD) was subcutaneously injected into the back of 6- to 8-week-old C57BL/6 mice (manufactured by SLC) ($MOG_{35-55}$ 200 µg/mouse). Next, the mice were intraperitoneally administered 200 ng of pertussis toxin (Ptx) (on day 0). On day 2, the mice were further intraperitoneally administered 200 ng of Ptx to induce EAE.

The EAE model mice were administered Compound 1 Salt (30 mg/kg in terms of free form) for a period of from day 1 to day 14. Pathological scores (EAE scores) of the mice were measured with time in accordance with Int. Immunol. 2012 November; 24(11): 681-91. doi: 10.1093/intimm/dxs075. The results are shown in FIG. 8.

Figure 8:
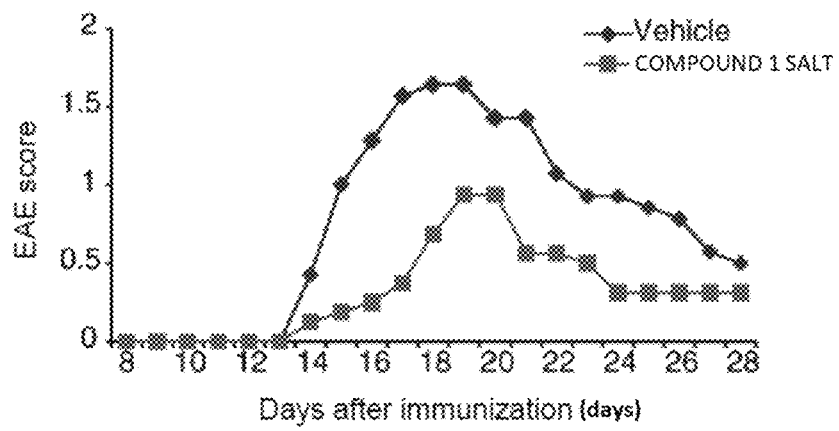
FIG. 8 is a graph for showing a time-dependent change in pathological score (EAE score) in an EAE model by Compound 1 Salt (Example 10).

The results of FIG. 8 revealed that the EAE scores were found to be significantly improved by Compound 1 Salt as compared to the control (Vehicle).

(Example 11) Therapeutic Effect of Compound 2 on Nasal Allergy

In this Example, a therapeutic effect of Compound 2 in a mouse actively-sensitized antibody-induced nasal allergy model serving as a nasal allergy model was confirmed. The mouse actively-sensitized antibody-induced nasal allergy model was generated by the following method. Seven-week-old BALB/c mice (manufactured by SLC, male) were initially sensitized by intraperitoneal administration of 200 µL of a mixed liquid of OVA (manufactured by Wako Pure Chemical Industries, Ltd.) (0.5 mg/mL) (100 µg/mouse), 5 mg/mL of aluminum hydroxide (ALUM; manufactured by Wako Pure Chemical Industries, Ltd.), and 1.5 µg/mL of pertussis toxin (manufactured by Wako Pure Chemical Industries, Ltd.). Next, 5 days after the initial sensitization, as additional sensitization, OVA (50 µg/mouse) was administered into the dorsal skin of the mice to perform systemic sensitization. After that, OVA (100 µg/mouse) was administered to the mice as nasal drops at a frequency of once a day as local sensitization for 8 days from day 18 after the initial sensitization to elicit a nasal allergy symptom due to active sensitization.

The model was orally administered Compound 2 (from 0.3 mg/kg to 3.0 mg/kg) daily from 3 days before the initial sensitization, and on the final day of the local sensitization, an effect of the test substance was evaluated using the number of times of nasal rubbing behavior in 1 hour as an indicator. A 0.5% (w/v) methylcellulose solution serving as a vehicle was used for a vehicle control group, and dexamethasone (manufactured by Tokyo Chemical Industry Co., Ltd.) was used for a positive control. The results are shown in FIG. 9.

Figure 9:
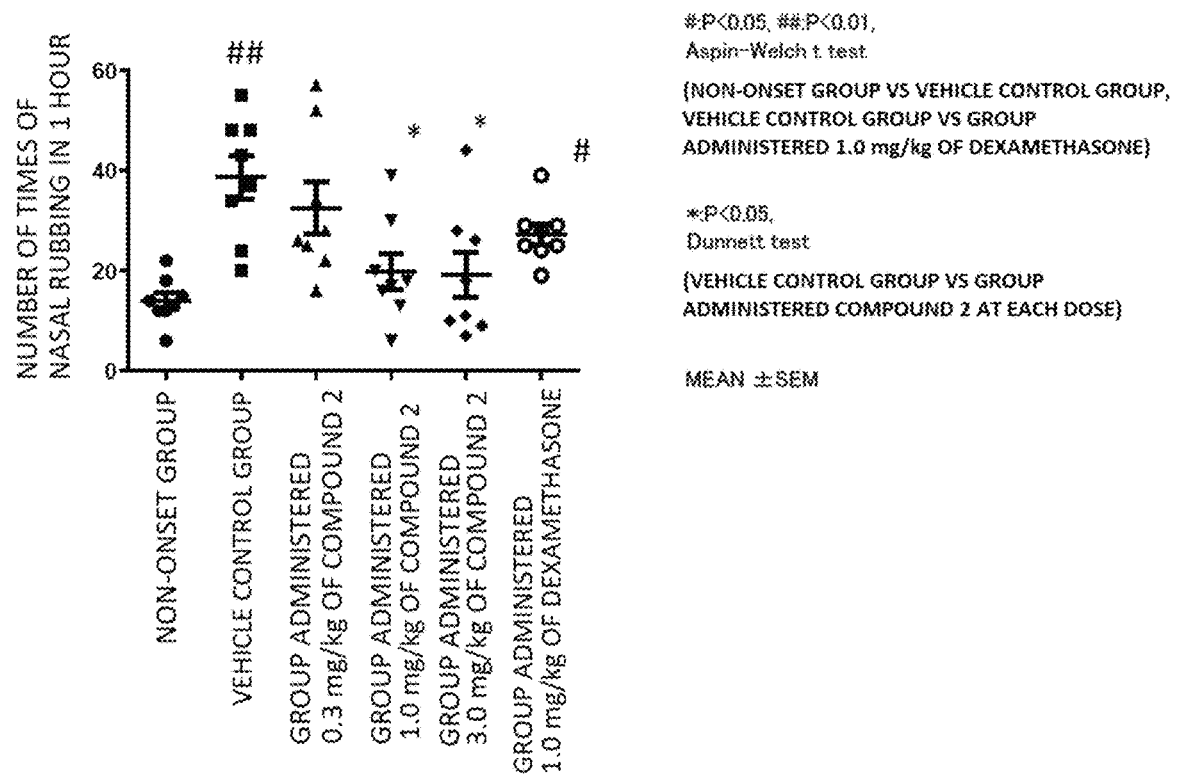
FIG. 9 is a graph for showing a suppressing action of Compound 2 on nasal rubbing in an actively-sensitized antibody-induced nasal allergy model (Example 11).

The results of FIG. 9 revealed that the administration of Compound 2 (1.0 mg/kg or 3.0 mg/kg) significantly suppressed the number of times of nasal rubbing.

(Example 12) Therapeutic Effects of Compound 2 on Increased Airway Resistance (Asthma)

In this Example, therapeutic effects of Compound 2 on an OVA-induced asthma model and a Th1-type asthma model serving as asthma models were confirmed.

(1) OVA-Induced Asthma

The OVA-induced asthma model was generated by the following method. Eight-week-old Balb/c mice (manufactured by Charles River Laboratories) were sensitized by intraperitoneal administration of 200 µL of physiological saline containing OVA (manufactured by SIGMA) (20 µg/mouse) and aluminum hydroxide (Alum; manufactured by LMS Co., Ltd.) (2.25 mg) on the day of initial sensitization and on day 8 and day 15 after the initial sensitization. After that, the mice were sensitized by inhalation of 1% OVA once a day through use of an ultrasonic nebulizer (manufactured by OMRON Corporation) to induce inflammation for consecutive 6 days from day 29 after the initial sensitization. A normal group similarly received intraperitoneal administration and inhalation of physiological saline.

The generated model received repeated oral administration of Compound 2 at a dose of 0.5 mg/kg once a day for a period of 34 days from the first day of the sensitization to the final induction day. Similarly, a vehicle control group and a positive control received repeated oral administration of a 0.5% (w/v) methylcellulose solution serving as a vehicle and 1 mg/kg of dexamethasone (manufactured by SIGMA), respectively. On the following day of the final antigen induction, for all the mice, airway reactivity was measured under an awake state using airway resistance after methacholine solution inhalation as an indicator. The mice were placed in an acrylic inhalation chamber, and received successive inhalation of physiological saline and 1.56 mg/mL, 3.125 mg/mL, 6.25 mg/mL, 12.5 mg/mL, and 25 mg/mL methacholine solutions for 1 minute each through use of a pressurized nebulizer (manufactured by PARI). After the inhalation of each solution, airway resistance (specific airway resistance: sRaw) was measured. An average of 100 breathes was adopted as individual sRaw at each measurement point. The sRaw was measured under an awake state by a double flow plethysmograph method using a comprehensive respiratory function measurement system (Pulmos-1; manufactured by M. I. P. S.). The results of the airway resistance measurement at the time of the inhalation of the 25 mg/mL methacholine solution are shown in FIG. 10A.

Figure 10A:
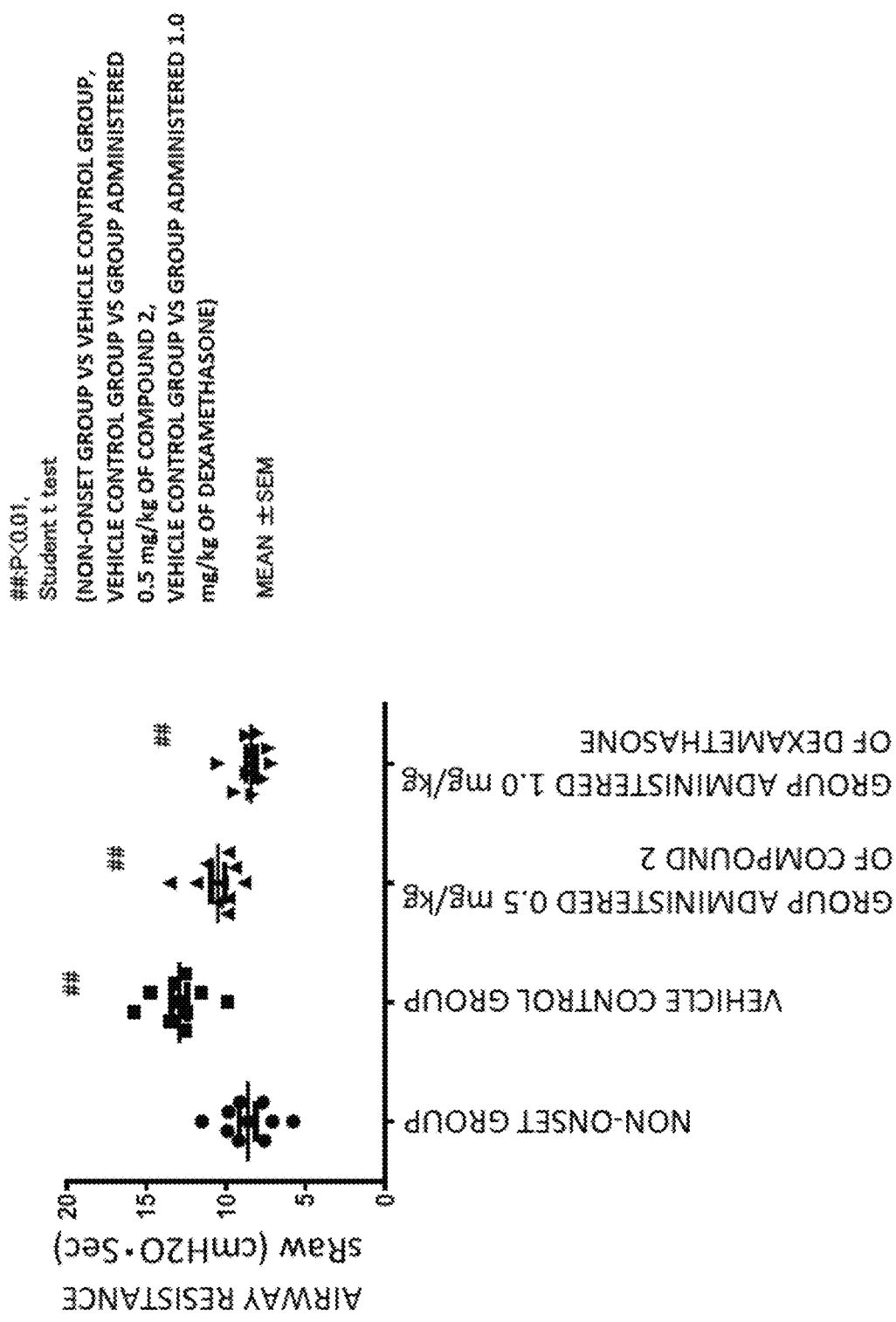
FIG. 10A is a graph for showing a suppressing action of Compound 2 on increased airway reactivity in an OVA-induced asthma model ((1) of Example 12).

The results of FIG. 10A revealed that the administration of Compound 2 suppressed an increase in airway reactivity.

(2) Th1-Type Asthma

The Th1-type asthma model was generated by the following method. Eight-week-old Balb/c mice (manufactured by Charles River Laboratories) were initially sensitized by single intraperitoneal administration of 200 μL of physiological saline containing endotoxin-free OVA (manufactured by Hyglos) (50 μg/mouse) and complete Freund's adjuvant (FCA; manufactured by Wako Pure Chemical Industries, Ltd.). After that, the mice were intranasally administered 50 μL of phosphate-buffered saline (PBS) containing endotoxin-free OVA (100 μg/mouse) and lipopolysaccharide (LPS, manufactured by SIGMA) (5 μg/mouse) to induce inflammation for consecutive 3 days from day 15 after the initial sensitization. A normal group received intraperitoneal administration of physiological saline and intranasal administration of PBS.

The generated model received repeated oral administration of Compound 2 at a dose of 0.5 mg/kg once a day for a period of 17 days from the first day of the sensitization to the final induction day. Similarly, a control group and a positive control received repeated oral administration of a 0.5% (w/v) methylcellulose solution serving as a vehicle and 1 mg/kg of dexamethasone (manufactured by SIGMA), respectively. On the following day of the final antigen induction (day 18), airway reactivity was measured in the same manner as in the section (1). The results of the airway resistance measurement at the time of the inhalation of the 25 mg/mL methacholine solution are shown in FIG. 10B.

Figure 10B:
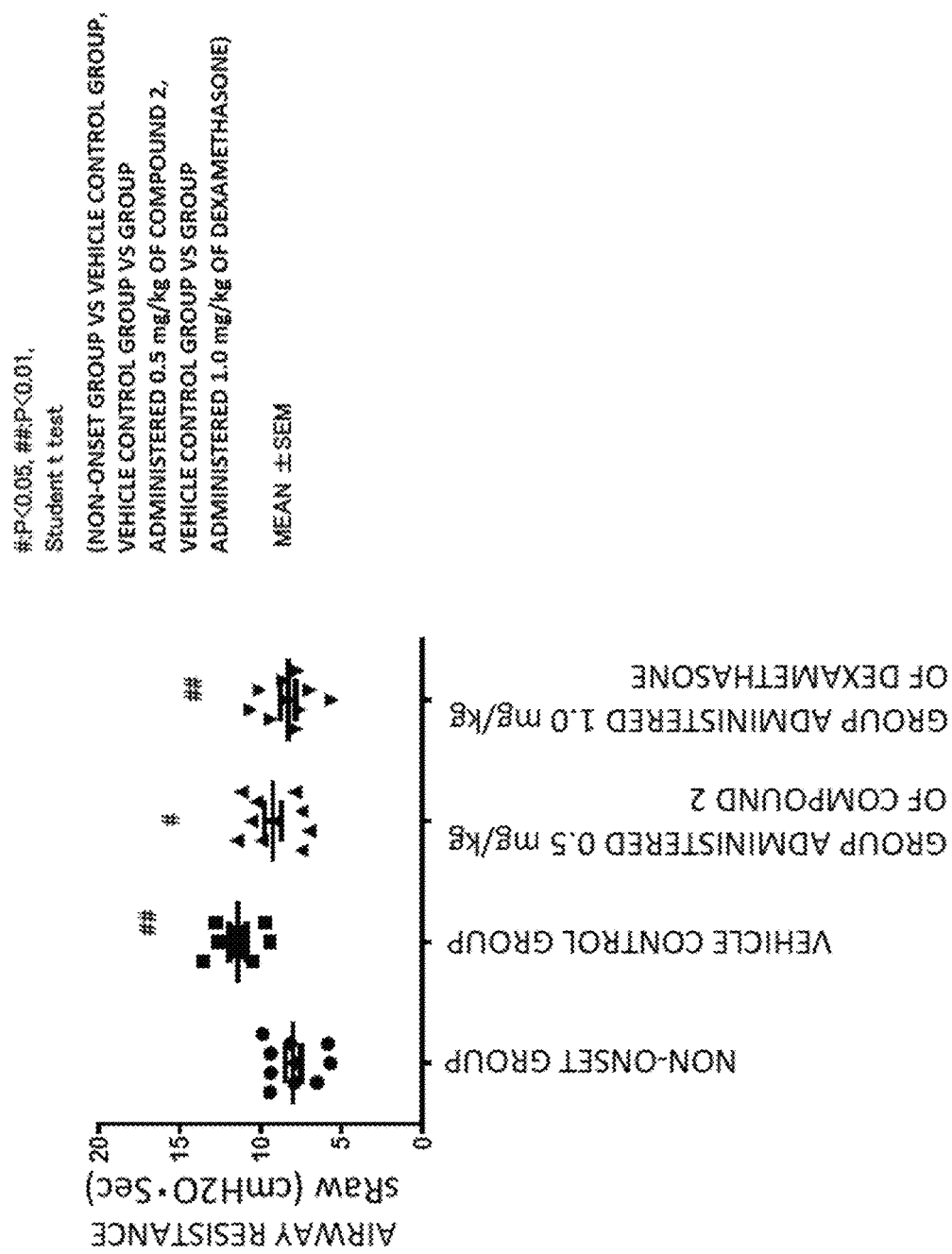
FIG. 10B is a graph for showing a suppressing action of Compound 2 on increased airway reactivity in a Th1-type asthma model ((2) of Example 12).

The results of FIG. 10B revealed that the administration of Compound 2 suppressed an increase in airway reactivity.

(Example 13) Therapeutic Effect of Infusion of Tregs Induced Ex Vivo on Contact Hypersensitivity In this Example, a therapeutic effect of infusion of Tregs induced ex vivo on a DNFB-induced contact hypersensitivity model was confirmed.

The Tregs were generated by the following method. Spleen cells derived from 12-week-old eFox mice were disrupted on a nylon mesh and filtered to prepare a cell suspension. Further, CD4$^+$ T cells ($1 \times 10^5$ cells) prepared from the cell suspension using CD4 Microbeads, Mouse (manufactured by Miltenyi Biotec) were cultured in the presence of an anti-CD3/CD28 antibody (Gibco Dynabeads Mouse T-Activator CD3/CD28; manufactured by Thermo Fisher Scientific) ($1 \times 10^5$ beads/mL), hTGF-β1 (manufactured by Peprotech) (5 ng/mL), mIL-2 (manufactured by R&D) (250 U/mL), and Compound 1 Salt (1 M) under a 5% $CO_2$ atmosphere at 37° C. for 3 days. After that, CD25 and Foxp3-GFP-positive T cells were acquired as the Tregs with FACSAria™ II (manufactured by BD).

The DNFB-induced contact hypersensitivity model was generated by the following method. Eight-week-old Balb/c mice (manufactured by SLC, female) were shaved on the abdomen, and then 25 μL of DNFB (0.5% (w/v) DNFB in acetone/olive oil (4/1), manufactured by Nacalai Tesque, Inc.) was applied thereto. On day 5 after the application of DNFB, the Tregs ($2 \times 10^4$ cells or $2 \times 10^5$ cells) acquired above were infused from the tail vein. Next, 20 μL of DNFB (0.3% (w/v) DNFB in acetone/olive oil (4/1)) was applied to the auricle to induce a contact hypersensitivity reaction. The contact hypersensitivity reaction was evaluated by measuring a change in auricle thickness using a constant pressure thickness gauge (manufactured by Teclock, PG-20).

As a result, when the Tregs induced by Compound 1 Salt were administered at $2 \times 10^5$ cells, an ear swelling of 220 μm was found in the mice on day 2 after the induction of the contact hypersensitivity reaction. In contrast, an ear swelling of 285 μm was found when the cells were not added. Through the administration of the Tregs induced by Compound 1 Salt to the DNFB-induced contact hypersensitivity model, the Tregs induced ex vivo were found to have a suppressing effect on a contact hypersensitivity response using an ear swelling as an indicator in a statistically significant manner (P<0.05; Dunnett's Multiple Comparison Test).

(Example 14) Induction from Naive T Cells to Tregs by Various CDK8/19 Inhibitory Drugs In this Example, induction from naive T cells to Tregs by various CDK8/19 inhibitory drugs was confirmed, and a Treg-inducing action was confirmed for a compound having CDK8 and/or CDK19 inhibitory activity.

The naive T cells were generated by the following method. Spleen was collected from 8 to 12-week-old C57BL6 mice (manufactured by SLC), and in the same manner as in Example 13, spleen cells were disrupted on a nylon mesh and filtered to prepare a cell suspension. Naive Th cells were prepared from the cell suspension using Naive CD4$^+$ T cell Isolation Kit, mouse (manufactured by Miltenyi Biotec). Biotin-Antibody Cocktail included with the kit was added to the spleen cells suspended in Minimum Essential Medium Eagle (MEM, manufactured by SIGMA), followed by incubation at 4° C. for 5 minutes. Further, Anti-Biotin MicroBeads and CD44 MicroBeads were added, followed by incubation at 4° C. for 10 minutes and then a centrifugation operation (300xg, 10 minutes). After the removal of the supernatant, the cells were resuspended in MEM and applied to an LS column (manufactured by Miltenyi Biotech). The cells contained in the flow-through liquid were used in the subsequent experiments. The prepared naive Th cells ($2 \times 10^5$ cells) were stimulated with an anti-CD3/CD28 antibody (Gibco Dynabeads Mouse T-Activator CD3/CD28;

manufactured by Thermo Fisher Scientific) in the presence of various CDK8/19 inhibitory drugs (usage amount: from 1 nM to 10,000 nM [[μM]]) at 5% $CO_2$ at 37° C. After having been cultured for 44 hours, the cells were stained using an anti-CD4 antibody (RM4-5; manufactured by eBioscience), an anti-CD25 antibody (7D4; manufactured by BD), an anti-Foxp3 antibody (FJK-165; manufactured by eBioscience), and flexible viability dye (manufactured by eBioscience). The stained cells were measured using Canto II (manufactured by BD) by a flow cytometry method, and a proportion of $CD25^+$ $Foxp3^+$ cells in $CD4^+$ viable cells was analyzed using FlowJo (manufactured by FlowJo). Further, when a proportion of $CD25^+$ $Foxp3^+$ cells in a solvent (0.1% DMSO)-added sample was defined as 100%, a compound concentration at which 150% of $CD25^+$ $Foxp3^+$ cells were obtained was defined as $EC_{150}$, an $EC_{150}$ value of each compound was calculated, and a geometric average was calculated based on data obtained from three trials. The results are shown in Table 2.

Table 2 revealed that the Tregs were induced in the naive Th cells by the various CDK8/19 inhibitory drugs.

TABLE 2

| CDK8/19 inhibitory drugs | $EC_{150}$ (nM) |
| --- | --- |
| Compound 1 Salt | 28.3 |
| Compound 2 | 10.2 |
| Senexin A | 192.2 |
| (R)-2-[5-(3-Chloro-4-hydroxyphenyl)-pyridin-3-ylamino]-2-phenylacetamide | 2.8 |

Senexin A: Proc. Natl. Acad. Sci. U.S.A. 109 13799-13804 (2012) (R)-2-[5-(3-Chloro-4-hydroxyphenyl)-pyridin-3-ylamino]-2-phen ylacetamide: Example 3 of WO 2014/029726 A1

(Example 15) In Vitro Induction of Foxp3 by Compound 1 Salt

In this Example, an ability to induce Foxp3 in $CD8^+$ T cells was confirmed for Compound 1 Salt produced in Example 1.

The lymph nodes of 6- to 8-week-old Foxp3-GFP fusion protein KI mice (eFox mice) were collected, and the tissue was disrupted using ground glass, and filtered through a nylon mesh to prepare a total lymphocytic cell suspension. eFox mice generated in accordance with a method described in Science. 2014 Oct. 17; 346(6207): 363-8. doi: 10.1126/science.1259077 were used as the eFox mice. The prepared total lymphocytic cells were stained with an anti-CD8 antibody (53-6.7; manufactured by BD), and $CD8^+$ T cells were prepared using FACSAria™ II (manufactured by BD).

Figure 11:
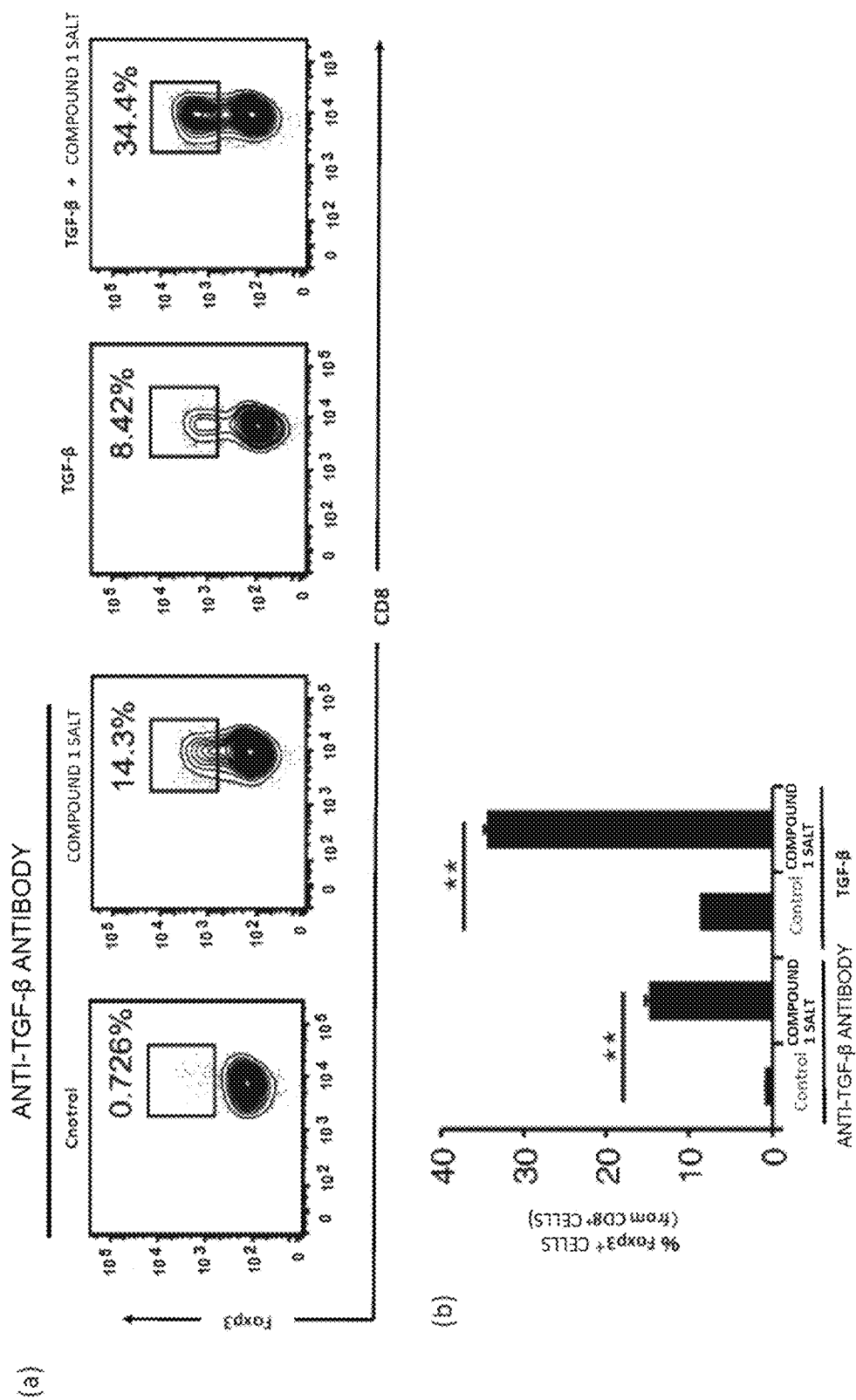
FIG. 11(a) are FACS analysis plots for showing the amounts of Foxp3 induced in Foxp3-negative CD8$^+$ T cells by Compound 1 Salt. The results of analysis in the case of adding an anti-TGF-β antibody are shown in the left of FIG. 11(a), and the results of analysis in the case of adding TGF-β are shown in the right of FIG. 11(a).
FIG. 11(b) is a graph for showing the amounts of Foxp3 obtained by the FACS analysis of FIG. 11(a) (Example 15).

As shown in the following items (i) to (iv), the prepared $CD8^+$ T cells ($2\times10^5$ cells) were stimulated using 5 μL of an anti-CD3/CD28 antibody (Gibco Dynabeads Mouse T-Activator CD3/CD28; manufactured by Thermo Fisher Scientific) in the presence/absence of 2 ng/mL of hTGF-β1 (manufactured by R&D) or 10 μg/mL of an anti-TGF-β antibody (manufactured by R&D) and 1 μM of Compound 1 Salt, and treated under a 5% $CO_2$ atmosphere at 37° C. for 72 hours.
(i) Anti-TGF-β antibody (control)
(ii) Anti-TGF-β antibody+Compound 1 Salt
(iii) hTGF-β1 (control)
(iv) hTGF-β1+Compound 1 Salt The cells after the treatment were stained with an anti-CD8 antibody (manufactured by BD), and a proportion of Foxp3-GFP-positive cells was analyzed by a flow cytometry method. The results are shown in FIG. 11(a). In addition, a graph for showing the results of the number (%) of those Foxp3-GFP-positive cells is shown in FIG. 11(b).

The results of FIG. 11(a) and FIG. 11(b) revealed that even under such a condition that TGF-β was blocked by the addition of the anti-TGF-β antibody, Foxp3 was significantly induced in the $CD8^+$ T cells by Compound 1 Salt alone. The results also revealed that Foxp3 was synergistically induced in the $CD8^+$ T cells by using Compound 1 Salt and TGF-β in combination.

(Example 16) Induction of Foxp3 by Compound 1 Salt in Human T Cells

In this Example, an ability to induce Foxp3 in human naive cells ($CD4^+$ $CCR7^+$ $CD45RA^+$) was confirmed for Compound 1 Salt produced in Example 1.

Human naive $CD4^+$ T cells ($CD4^+$ $CCR7^+$ $CD45RA^+$) were prepared from human peripheral blood cells (manufactured by Lifeline cell technology, manufactured by Stemcell technologies) using Human naive $CD4^+$ T Cell Isolation kit (manufactured by Miltenyi Biotec). The prepared human naive T cells ($2\times10^5$ cells) were stimulated using an anti-CD3/CD28 antibody (Gibco Dynabeads Human T-Activator CD3/CD28; manufactured by Thermo Fisher Scientific) ($2\times10^5$ beads), and treated in the presence/absence of Compound 1 Salt (10 nM, 100 nM, or 1,000 nM) under a 5% $CO_2$ atmosphere at 37° C. for 4 days.

Figure 12:
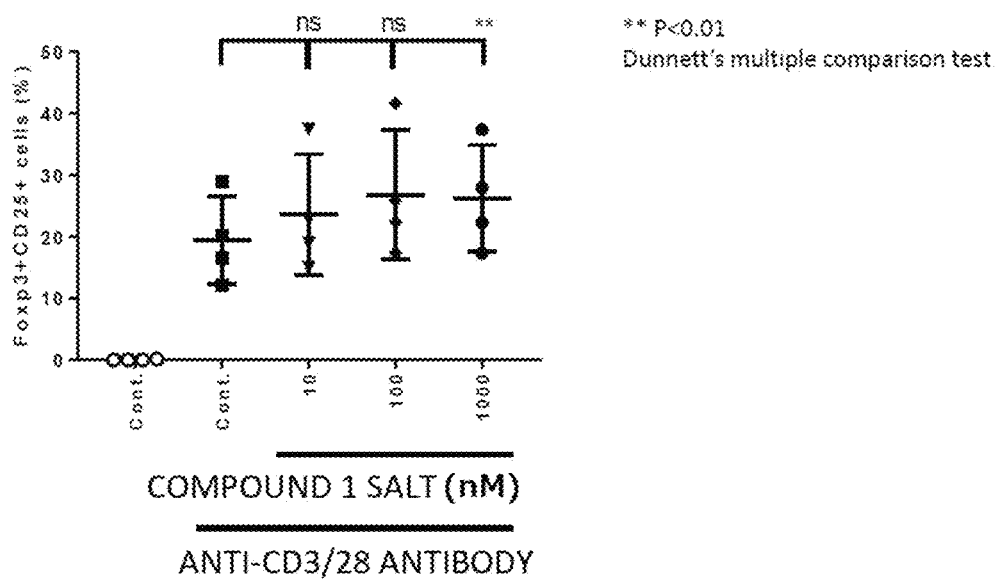
FIG. 12 is a graph for showing the results of induction of Foxp3$^+$CD25$^+$ cells (%) in human naive T cells by Compound 1 Salt (Example 16).

The cells after the treatment were stained with Fixable viability dye (manufactured by eBioscience), an anti-CD4 antibody (RPA-T4: manufactured by eBioscience), an anti-CD25 antibody (BC96: manufactured by eBioscience), and an anti-Foxp3 antibody (236A/E7: manufactured by eBioscience), and measured using Canto II (manufactured by BD) by a flow cytometry method. Further, a proportion of $Foxp3^+CD25^+$ cells in $CD4^+$ viable cells was analyzed using FlowJo (manufactured by FlowJo). The proportion (%) of $Foxp3^+CD25^+$ cells is shown in FIG. 12. The results of FIG. 12 revealed that Compound 1 Salt induced Foxp3 in the human naive $CD4^+$ T cells.

(Example 17) Induction of Foxp3 by Compound 1 Salt in Human T Cells

In this Example, an ability to induce Foxp3 in human naive cells ($CD4^+$ $CD25^-$ $CD45RA^+$ $Foxp3^-$) was confirmed for Compound 1 Salt produced in Example 1.

Human peripheral blood mononuclear cells (manufactured by Wako Pure Chemical Industries, Ltd.) were stained using an anti-CD4 antibody (RPA-T4; manufactured by BD), an anti-CD25 antibody (M-A251; manufactured by BD), and an anti-CD45RA antibody (HI100; manufactured by BD), and human naive $CD4^+$ T cells ($CD4^+$ $CD25^-$ $CD45RA^+$ $Foxp3^-$) were prepared using FACSAria™ II (manufactured by BD). The prepared human naive T cells ($1\times10^5$ cells) were stimulated using an anti-CD3/CD28 antibody (Gibco Dynabeads Human T-Activator CD3/CD28; manufactured by Thermo Fisher Scientific) ($2\times10^5$ beads), and treated in the presence/absence of hIL-2 (manufactured by Shionogi & Co., Ltd.) (50 U/ml) and Compound 1 Salt (10 nM or 100 nM) under a 5% $CO_2$ atmosphere at 37° C. for 4 days.

Figure 13:
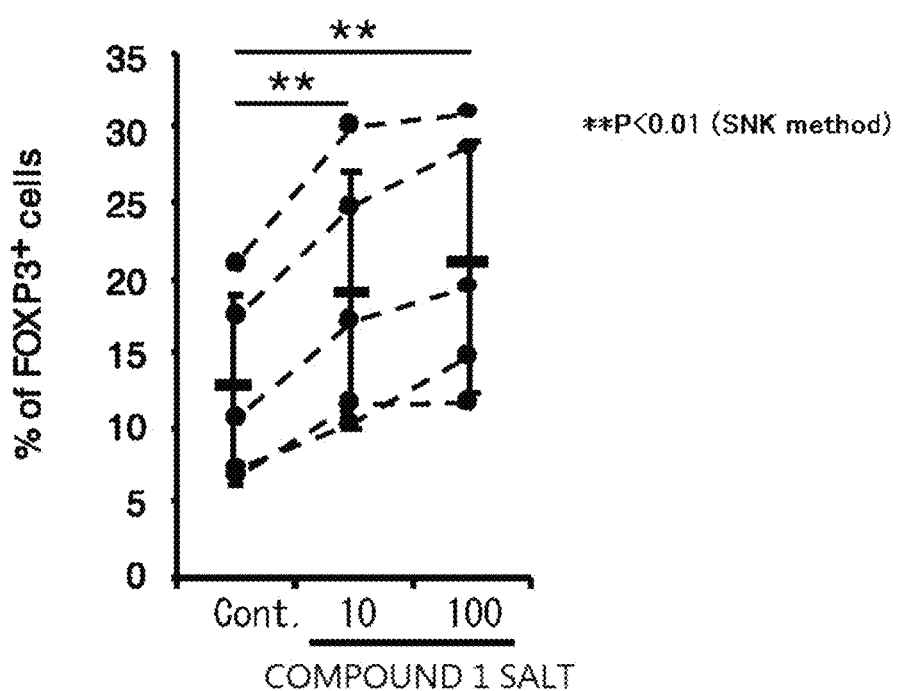
FIG. 13 is a graph for showing the results of Foxp3 induction in human naive T cells by Compound 1 Salt (Example 17).

The cells after the treatment were stained with Fixable viability dye (manufactured by eBioscience), an anti-CD4 antibody (manufactured by BD), and an anti-Foxp3 antibody (manufactured by eBioscience), and a proportion of Foxp3- positive cells in the CD4+ T cells was analyzed by a flow cytometry method. The proportion (%) of Foxp3-positive cells is shown in FIG. 13. The results of FIG. 13 revealed that Compound 1 Salt induced Foxp3 in the human naive CD4+ T cells.

(Example 18) Induction of Foxp3 by Compound 1 Salt in Human CD4 T+ Cells

In this Example, an ability to induce Foxp3 in human CD4 cells was confirmed for Compound 1 Salt produced in Example 1.

(1) Induction of Foxp3 in Naive T Cells

Figure 14:
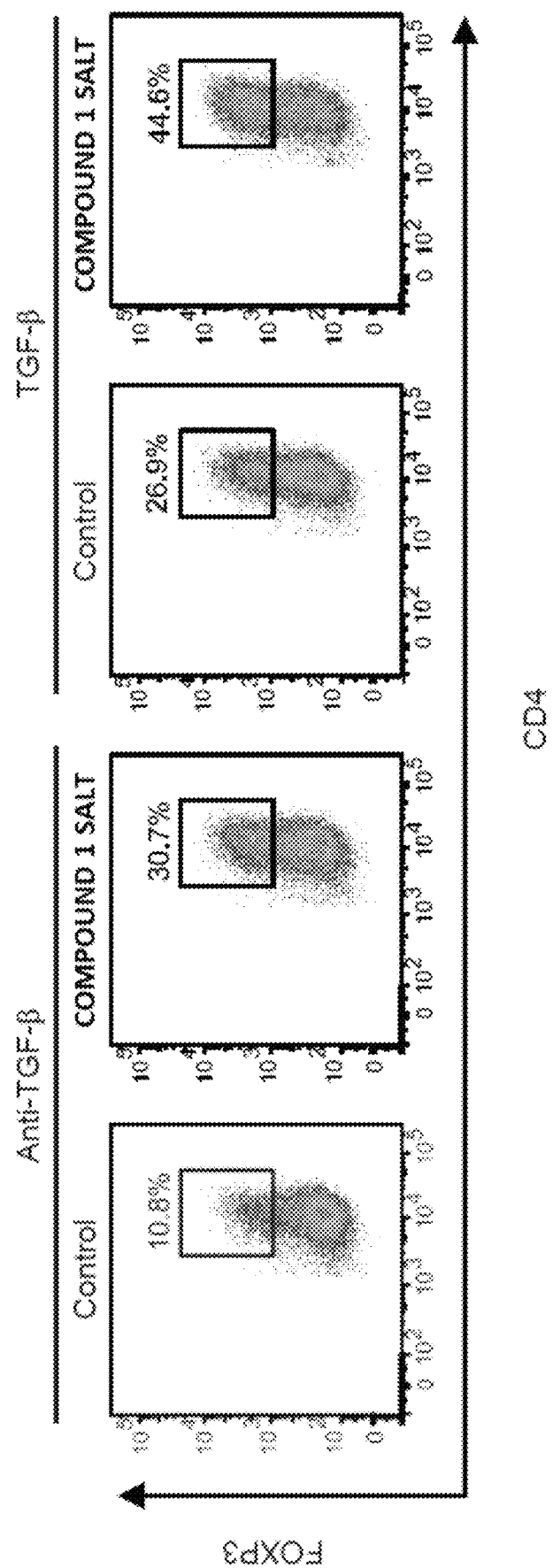
FIG. 14(a) are FACS analysis plots for showing the amounts of Foxp3 induced in human naive CD4$^+$ T cells by Compound 1 Salt. The results of analysis in the case of adding an anti-TGF-β antibody are shown in the left of FIG. 14(a), and the results of analysis in the case of adding TGF-β are shown in the right of FIG. 14(a).
FIG. 14(b) is a graph for showing the amounts of Foxp3 obtained by the FACS analysis of FIGS. 14(a) ((1) of Example 18).
Figure 14:
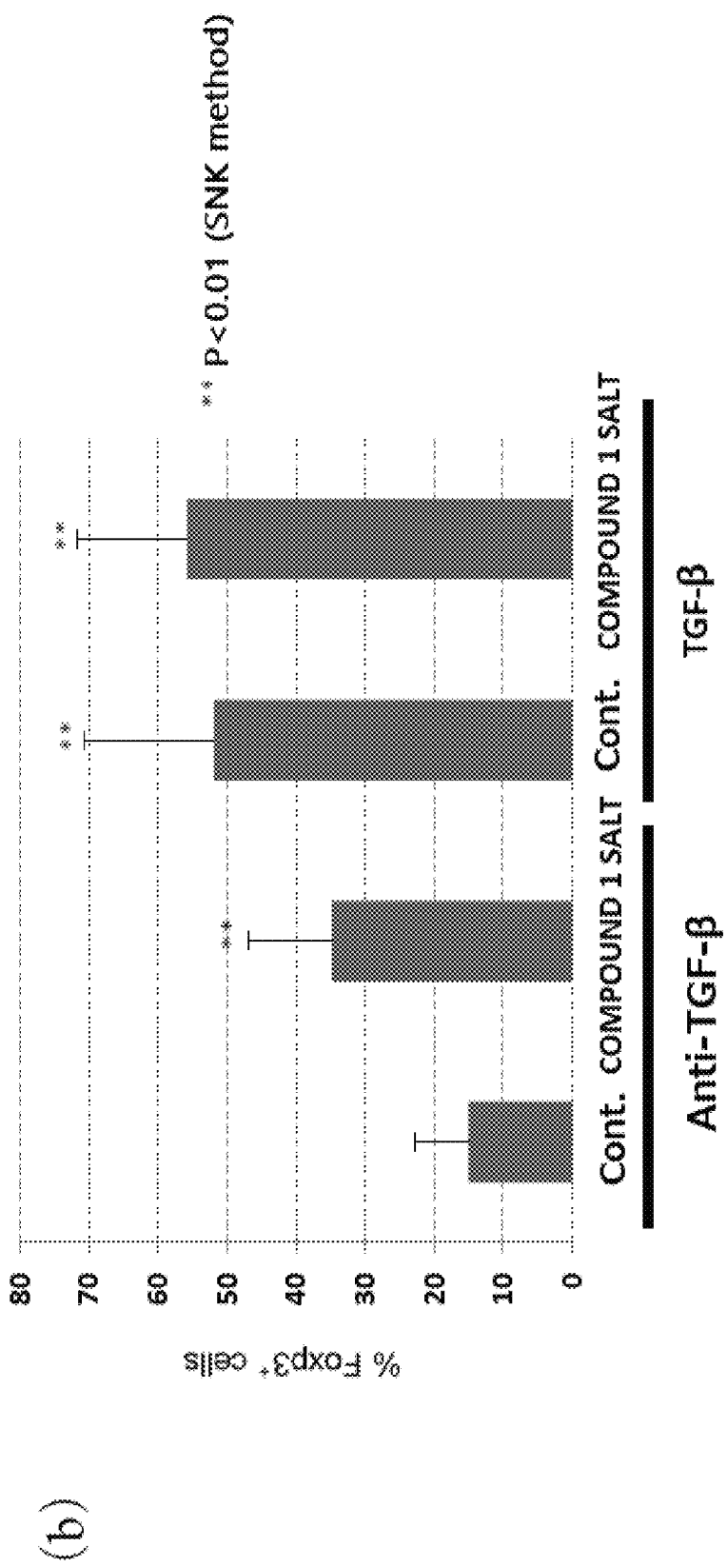

Human naive CD4+ T cells (CD4+ CD25- CD45RA+ Foxp3-) were prepared from human peripheral blood mononuclear cells (manufactured by Wako Pure Chemical Industries, Ltd.) in the same manner as in Example 17. As shown in the following items (i) to (iv), the prepared naive T cells ($2\times10^5$ cells) were stimulated using 5 μL of an anti-CD3/CD28 antibody (Gibco Dynabeads Human T-Activator CD3/CD28; manufactured by Thermo Fisher Scientific) in the presence/absence of 2 ng/mL of hTGF-β1 (manufactured by R&D) or 10 μg/mL of an anti-TGF-β antibody (manufactured by R&D), hIL-2 (manufactured by Shionogi & Co., Ltd.) (50 U/ml), and 100 nM of Compound 1 Salt, and treated under a 5% $CO_2$ atmosphere at 37° C. for 72 hours.
(i) Anti-TGF-β antibody (control)
(ii) Anti-TGF-β antibody+Compound 1 Salt
(iii) hTGF-β1 (control)
(iv) hTGF-β1+Compound 1 Salt The cells after the treatment were stained with an anti-CD4 antibody (manufactured by BD) and an anti-Foxp3 antibody (manufactured by eBioscience), and a proportion of Foxp3-positive cells was analyzed by a flow cytometry method. The results are shown in FIG. 14(a). In addition, the number (%) of those Foxp3-positive cells is shown in FIG. 14(b).

The results of FIG. 14(a) and FIG. 14(b) revealed that even under such a condition that TGF-β was blocked by the addition of the anti-TGF-β antibody, Foxp3 was significantly induced in the naive T cells by Compound 1 Salt alone (control: 10.8%, Compound 1 Salt treatment: 30.7%). The results also revealed that Foxp3 was synergistically induced in the naive T cells by using Compound 1 Salt and TGF-β in combination (TGF-β: 26.9%, TGF-β+Compound 1 treatment: 44.6%).

(2) Induction of Foxp3 in Effector Memory T Cells

Figure 15:
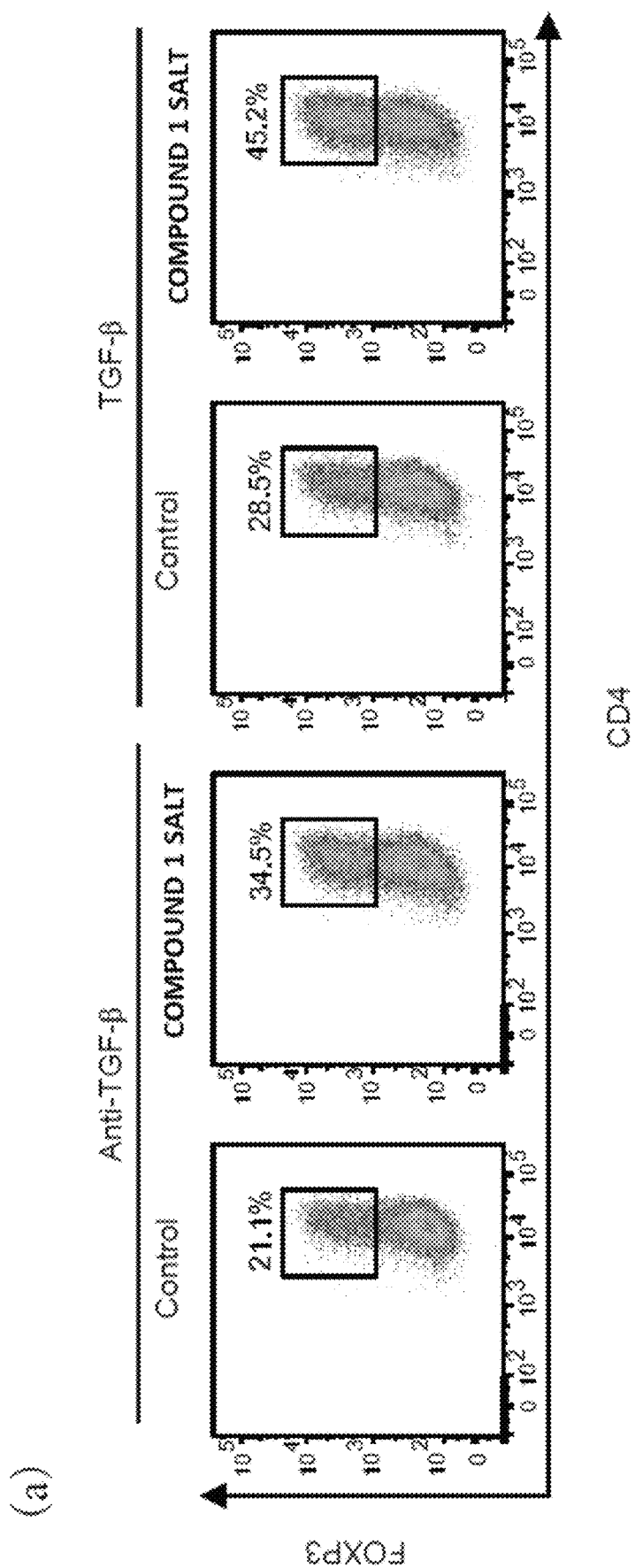
FIG. 15(a) are FACS analysis plots for showing the amounts of Foxp3 induced in human effector memory CD4$^+$ T cells by Compound 1 Salt. The results of analysis in the case of adding an anti-TGF-β antibody are shown in the left of FIG. 15(a), and the results of analysis in the case of adding TGF-β are shown in the right of FIG. 15(a).
FIG. 15(b) is a graph for showing the amounts of Foxp3 obtained by the FACS analysis of FIG. 15(a) ((2) of Example 18).
Figure 15:
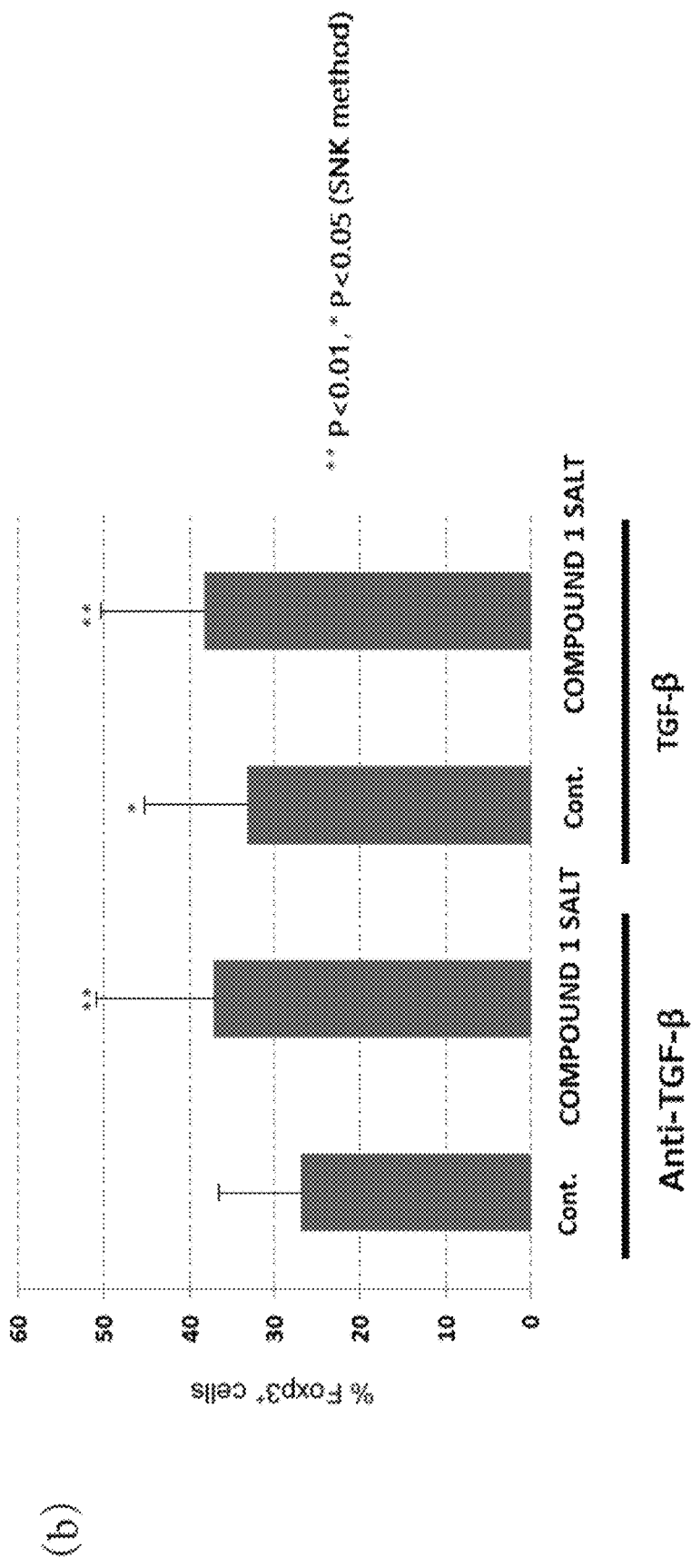

Human peripheral blood mononuclear cells (manufactured by Wako Pure Chemical Industries, Ltd.) were stained using an anti-CD4 antibody (RPA-T4; manufactured by BD), an anti-CD25 antibody (M-A251; manufactured by BD), and an anti-CD45RA antibody (HI100; manufactured by BD), and human effector memory CD4+ T cells (CD4+ CD25- CD45RA- Foxp3-) were prepared using FACSAria™ II (manufactured by BD). As shown in the following items (i) to (iv), the prepared effector memory T cells ($2\times10^5$ cells) were stimulated using 5 μL of an anti-CD3/CD28 antibody (Gibco Dynabeads Human T-Activator CD3/CD28; manufactured by Thermo Fisher Scientific) in the presence/absence of 2 ng/mL of hTGF-11 (manufactured by R&D) or 10 μg/mL of an anti-TGF-β antibody (manufactured by R&D), hIL-2 (manufactured by Shionogi & Co., Ltd.) (50 U/ml), and 100 nM of Compound 1 Salt, and treated under a 5% $CO_2$ atmosphere at 37° C. for 72 hours.
(i) Anti-TGF-β antibody (control)
(ii) Anti-TGF-β antibody+Compound 1 Salt
(iii) hTGF-β1 (control)
(iv) hTGF-β1+Compound 1 Salt The cells after the treatment were stained with an anti-CD4 antibody (manufactured by BD) and an anti-Foxp3 antibody (manufactured by eBioscience), and a proportion of Foxp3-positive cells was analyzed by a flow cytometry method. The results are shown in FIG. 15(a). In addition, the number (%) of those Foxp3-positive cells is shown in FIG. 15(b).

The results of FIG. 15(a) and FIG. 15(b) revealed that even under such a condition that TGF-β was blocked by the addition of the anti-TGF-β antibody, Foxp3 was significantly induced in the effector memory T cells by Compound 1 Salt alone (control: 21.1%, Compound 1 Salt treatment: 34.5%). The results also revealed that Foxp3 was synergistically induced in the effector memory T cells by using Compound 1 Salt and TGF-β in combination (TGF-β: 28.5%, TGF-β+Compound 1 treatment: 45.2%).

(Example 19) Induction of Foxp3 by Compound 1 Salt in Human CD8 T+ Cells

In this Example, an ability to induce Foxp3 in human CD8+ T cells was confirmed for Compound 1 Salt produced in Example 1.

(1) Induction of Foxp3 in Naive T Cells

Human peripheral blood mononuclear cells (manufactured by Wako Pure Chemical Industries, Ltd.) were stained using an anti-CD8 antibody (53-6.7; manufactured by BD), an anti-CD25 antibody (M-A251; manufactured by BD), and an anti-CD45RA antibody (HI100; manufactured by BD), and human naive CD8+ T cells (CD8+ CD25- CD45RA+ Foxp3-) were prepared using FACSAria™ II (manufactured by BD). As shown in the following items (i) to (iv), the prepared naive T cells ($1\times10^5$ cells) were stimulated using 5 μL of an anti-CD3/CD28 antibody (Gibco Dynabeads Human T-Activator CD3/CD28; manufactured by Thermo Fisher Scientific) in the presence/absence of 2 ng/mL of hTGF-β1 (manufactured by R&D) or 10 μg/mL of an anti-TGF-β antibody (manufactured by R&D), hIL-2 (manufactured by Shionogi & Co., Ltd.) (50 U/ml), and 100 nM of Compound 1 Salt, and treated under a 5% $CO_2$ atmosphere at 37° C. for 72 hours.
(i) Anti-TGF-β antibody (control)
(ii) Anti-TGF-β antibody+Compound 1 Salt
(iii) hTGF-β1 (control)
(iv) hTGF-β1+Compound 1 Salt The cells after the treatment were stained with an anti-CD8 antibody (manufactured by BD) and an anti-Foxp3 antibody (manufactured by eBioscience), and a proportion of Foxp3-positive cells was analyzed by a flow cytometry method. The proportion (%) of Foxp3-positive cells is shown in FIG. 16.

Figure 16:
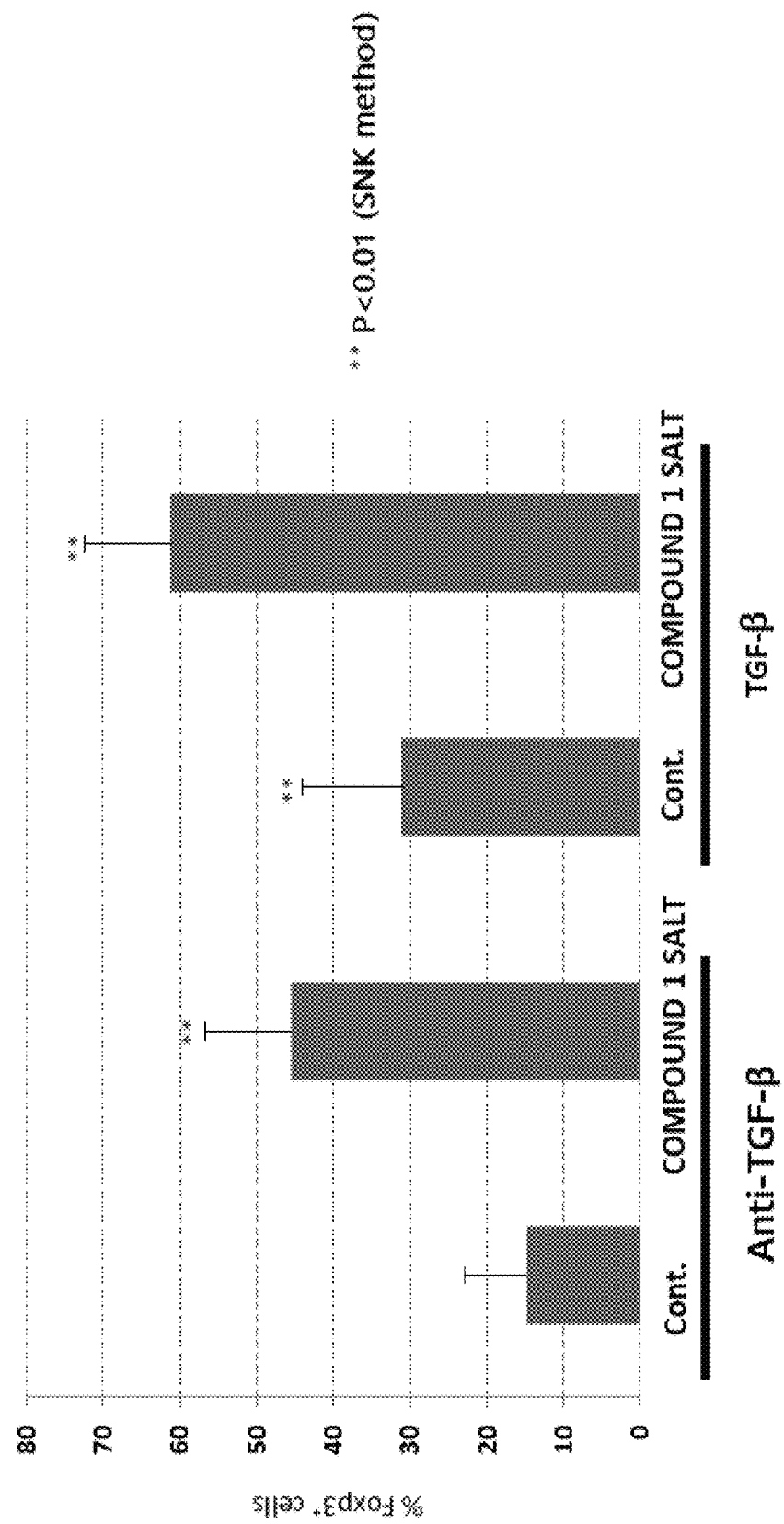
FIG. 16 is a graph for showing the results of induction of Foxp3 in human naive CD8$^+$ T cells by Compound 1 Salt ((1) of Example 19).

The results of FIG. 16 revealed that even under such a condition that TGF-β was blocked by the addition of the anti-TGF-β antibody, Foxp3 was significantly induced in the naive T cells by Compound 1 Salt alone. The results also revealed that Foxp3 was synergistically induced in the naive T cells by using Compound 1 Salt and TGF-β in combination.

(2) Induction of Foxp3 in Effector Memory T Cells

Human peripheral blood mononuclear cells (manufactured by Wako Pure Chemical Industries, Ltd.) were stained using an anti-CD8 antibody (53-6.7; manufactured by BD), an anti-CD25 antibody (M-A251; manufactured by BD), and an anti-CD45RA antibody (HI100; manufactured by BD), and human effector memory CD8$^+$ T cells (CD8$^+$ CD25$^-$ CD45RA$^-$ Foxp3$^-$) were prepared using FACSAria™ II (manufactured by BD). As shown in the following items (i) to (iv), the prepared effector memory T cells (1×10$^5$ cells) were stimulated using 5 μL of an anti-CD3/CD28 antibody (Gibco Dynabeads Human T-Activator CD3/CD28; manufactured by Thermo Fisher Scientific) in the presence/absence of 2 ng/mL of hTGF-β1 (manufactured by R&D) or 10 μg/mL of an anti-TGF-1 antibody (manufactured by R&D), hIL-2 (manufactured by Shionogi & Co., Ltd.) (50 U/ml), and 100 nM of Compound 1 Salt, and treated under a 5% CO$_2$ atmosphere at 37° C. for 72 hours.
(i) Anti-TGF-β antibody (control)
(ii) Anti-TGF-β antibody+Compound 1 Salt
(iii) hTGF-β1 (control)
(iv) hTGF-β1+Compound 1 Salt The cells after the treatment were stained with an anti-CD8 antibody (manufactured by BD) and an anti-Foxp3 antibody (manufactured by eBioscience), and a proportion of Foxp3-positive cells was analyzed by a flow cytometry method. The proportion (%) of those Foxp3-positive cells is shown in FIG. 17.

Figure 17:
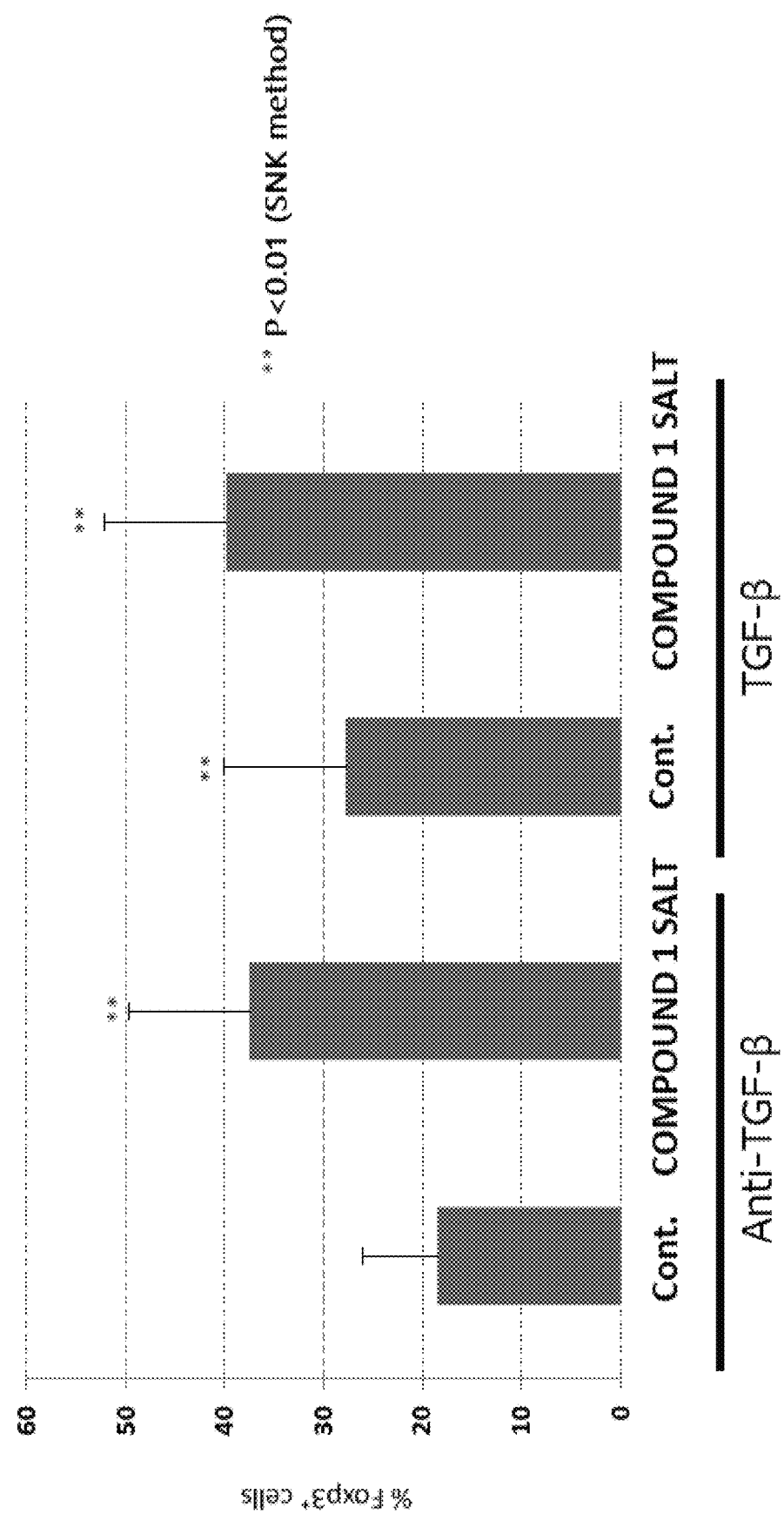
FIG. 17 is a graph for showing the results of induction of Foxp3 in human effector memory CD8$^+$ T cells by Compound 1 Salt ((2) of Example 19). an antigen (OVA) to the mice is shown in the right of FIG. 6(a).

The results of FIG. 17 revealed that even under such a condition that TGF-β was blocked by the addition of the anti-TGF-β antibody, Foxp3 was significantly induced in the effector memory T cells by Compound 1 Salt alone. The results also revealed that Foxp3 was synergistically induced in the effector memory T cells by using Compound 1 Salt and TGF-β in combination.

The invention claimed is:

1. A compound selected from 4-[1-(2-methyl-1H-benzimidazol-5-yl)-1H-imidazo[4,5-c]pyridin-2-yl]-1,2,5-oxadiazol-3-amine and 3-{1-[1-(4-methoxyphenyl)piperidin-4-yl]-4-methyl-1H-imidazo[4,5-c]pyridin-2-yl}pyrazin-2-amine, or a salt, a hydrate, or a solvate thereof.

2. A pharmaceutical composition comprising as an active ingredient a compound selected from 4-[1-(2-methyl-1H-benzimidazol-5-yl)-1H-imidazo[4,5-c]pyridin-2-yl]-1,2,5-oxadiazol-3-amine and 3-{1-[1-(4-methoxyphenyl)piperidin-4-yl]-4-methyl-1H-imidazo[4,5-c]pyridin-2-yl}pyrazin-2-amine, or a salt, a hydrate, or a solvate thereof, and said pharmaceutical composition further comprising a carrier or an excipient.

3. A Foxp3 inducer for producing regulatory T cells from T cells, comprising as an active ingredient the compound of claim 1.

4. The Foxp3 inducer according to claim 3, wherein the T cells comprise CD4$^+$ Foxp3$^-$ T cells.

5. The Foxp3 inducer according to claim 3, wherein the T cells comprise CD4$^+$ CD25$^-$ Foxp3$^-$ T cells.

6. The Foxp3 inducer according to claim 3, wherein the T cells comprise CD8$^+$ Foxp3$^-$ T cells.

7. The pharmaceutical composition of claim 2, wherein said excipient is lactose, mannitol, glucose, hydroxypropyl cellulose, microcrystalline cellulose, starch, polyvinylpyrrolidone, or magnesium aluminometasilicate or any combinations thereof.

8. The pharmaceutical composition of claim 2, further comprising a lubricant or a disintegrant.

9. A production method for regulatory T cells, comprising treating T cells with a) the compound of claim 1 or b) an siRNA of CDK8 or CDK19.

10. A production method for regulatory T cells, comprising subjecting T cells to T cell receptor (TCR) stimulation in the presence of a) the compound of claim 1 or b) an siRNA of CDK8 or CDK19.

11. The production method for regulatory T cells according to claim 10, wherein the TCR stimulation is performed in the presence of TGF-β, rapamycin, or retinoic acid.

12. The production method for regulatory T cells according to claim 9, wherein the T cells comprise CD4$^+$ Foxp3$^-$ T cells.

13. The production method for regulatory T cells according to claim 9, wherein the T cells comprise CD4$^+$ CD25$^-$ Foxp3$^-$ T cells.

14. The production method for regulatory T cells according to claim 9, wherein the T cells comprise CD8$^+$ Foxp3$^-$ T cells.

* * * * *